(12) United States Patent
Van Der Vliet et al.

(10) Patent No.: US 11,384,145 B2
(45) Date of Patent: Jul. 12, 2022

(54) IMMUNOGLOBULINS BINDING HUMAN Vγ9Vδ2 T CELL RECEPTORS

(71) Applicant: LAVA THERAPEUTICS N.V., Utrecht (NL)

(72) Inventors: Johannes Jelle Van Der Vliet, Utrecht (NL); Renée Cornelia Gerarda De Bruin, Utrecht (NL); Tanja Denise De Gruijl, Utrecht (NL); Hendrik Marinus Willem Verheul, Utrecht (NL)

(73) Assignee: LAVA THERAPEUTICS N.V., Utrecht (NL)

( * ) Notice: Subject to any disclaimer, the term of this patent is extended or adjusted under 35 U.S.C. 154(b) by 0 days.

(21) Appl. No.: 17/513,621

(22) Filed: Oct. 28, 2021

(65) Prior Publication Data

US 2022/0098301 A1   Mar. 31, 2022

Related U.S. Application Data

(63) Continuation of application No. 16/414,424, filed on May 16, 2019, which is a continuation of application No. 15/302,927, filed as application No. PCT/NL2015/050235 on Apr. 10, 2015, now Pat. No. 10,501,540.

(30) Foreign Application Priority Data

Apr. 10, 2014   (NL) .................................... 2012604

(51) Int. Cl.
*A61P 35/00*   (2006.01)
*C07K 16/28*   (2006.01)

(52) U.S. Cl.
CPC ...... *C07K 16/2809* (2013.01); *C07K 2317/21* (2013.01); *C07K 2317/22* (2013.01); *C07K 2317/565* (2013.01); *C07K 2317/569* (2013.01); *C07K 2317/622* (2013.01); *C07K 2317/70* (2013.01); *C07K 2317/75* (2013.01); *C07K 2317/76* (2013.01)

(58) Field of Classification Search
None
See application file for complete search history.

(56) References Cited

FOREIGN PATENT DOCUMENTS

WO   WO-2004062551 A2 *   7/2004   ........... A61K 38/166

OTHER PUBLICATIONS

Vincke et al. (JBC, vol. 284, No. 5, pp. 3273-3284, Jan. 30, 2009). (Year: 2009).*

* cited by examiner

*Primary Examiner* — Zachary S Skelding
(74) *Attorney, Agent, or Firm* — Cooley LLP

(57) ABSTRACT

The invention is in the field of medicine and relates to immunology, and relates in particular to human Vγ9Vδ2 T cell receptor binding immunoglobulin molecules. Human Vγ9Vδ2 T cell receptor binding immunoglobulin molecules are in particular for use in medical treatment and/or useful in assays with human Vγ9Vδ2 T cells, wherein human Vγ9Vδ2 T cells may be modulated.

21 Claims, 8 Drawing Sheets

Figure 1:
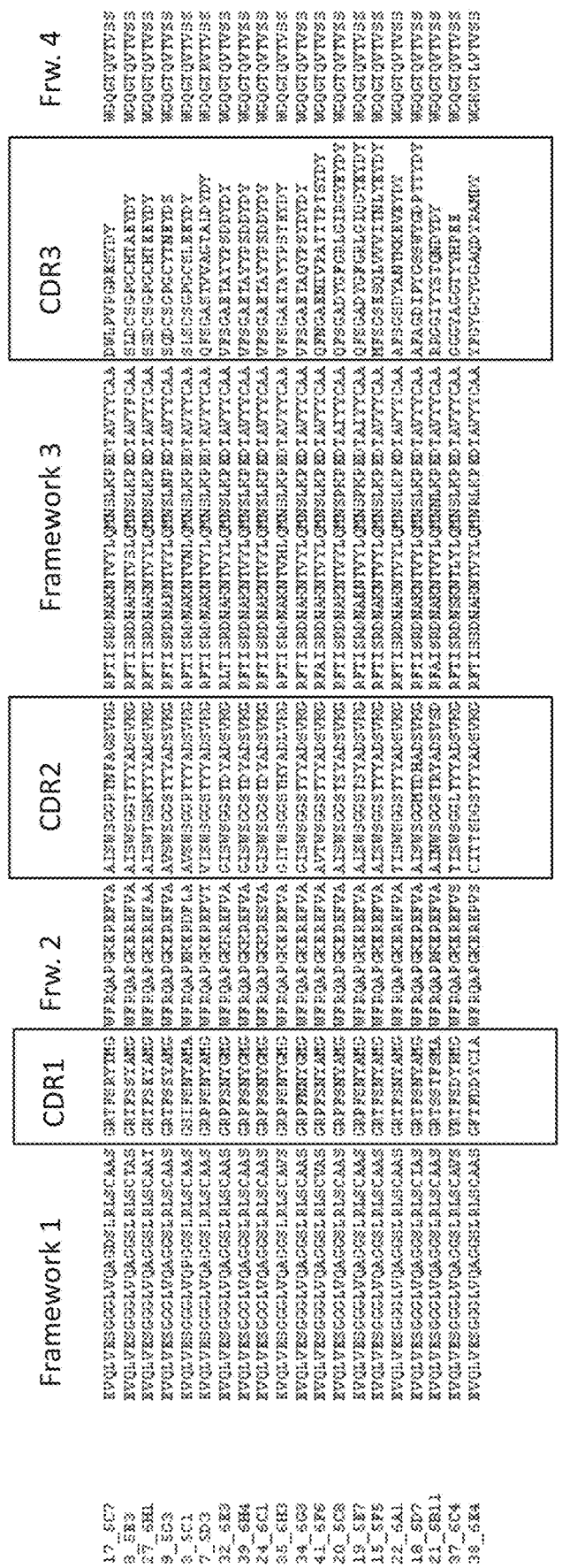

Specification includes a Sequence Listing.

IMMUNOGLOBULINS BINDING HUMAN Vγ9Vδ2 T CELL RECEPTORS

CROSS-REFERENCE TO RELATED APPLICATIONS

This application is a continuation of U.S. patent application Ser. No. 16/414,424, filed May 16, 2019, which is a continuation of U.S. patent application Ser. No. 15/302,927, filed Oct. 7, 2016 (issued as U.S. Pat. No. 10,501,540), which is a U.S. National Stage Application under 35 U.S.C. § 371 of International Application No. PCT/NL2015/050235, filed Apr. 10, 2015, which claims the benefit of the Netherlands Patent Application No. 2012604, filed Apr. 10, 2014, the disclosures of which are hereby incorporated by reference in their entireties for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: LVAT_001_02US_SeqList_ST25.txt, date recorded Oct. 28, 2021, file size 38 kilobytes).

FIELD OF THE INVENTION

The present invention is in the field of medicine and relates to immunology. The invention relates to immunoglobulins binding T cells. In particular, the invention relates to immunoglobulins binding human Vγ9Vδ2 T cell receptors. The invention provides for immunoglobulin molecules that bind a human Vγ9Vδ2 T cell receptor, such as antibodies, single chain antibodies, or single domain antibodies, wherein the human Vγ9Vδ2 T cells may be modulated.

BACKGROUND

The majority of γε peripheral blood lymphocytes (PBLs) in human adults express T-cell receptors (TCRs) comprising Vγ9 and Vδ2 regions. Vγ9Vδ2 T cells can react against a wide array of pathogens and tumour cells. This broad reactivity is understood to be conferred by phosphoantigens which are able to specifically activate this T-cell subset in a TCR dependent fashion. The broad antimicrobial and anti-tumour reactivity of Vγ9Vδ2 T-cells suggest a direct involvement in immune control of cancers and infections. In addition to fighting disease, in some diseases or medical treatment Vγ9Vδ2 T cells may be overstimulated or inadvertently activated.

Hence, agents that can activate Vγ9Vδ2 T cells can be useful in the treatment of infections or cancer as these may promote Vγ9Vδ2 T cell reactivity towards the pathogen or infected cells or cancer. Furthermore, agents that block activation of Vγ9Vδ2 T cells may be useful in diseases or medical treatment where it is advantageous to reduce Vγ9Vδ2 T cell activation, i.e. wherein Vγ9Vδ2 T cells are overstimulated or inadvertently activated. Finally, agents that can bind a Vγ9Vδ2 T cell, but do not have an effect on (phosphoantigen) activation of Vγ9Vδ2 T cells are useful for labelling cells, for example for selecting or identifying Vγ9Vδ2 T cells. Hence, there is a need in the art to provide for agents that can bind to Vγ9Vδ2 T cells, and for agents that can block phosphoantigen activation of Vγ9Vδ2 T cells or can activate Vγ9Vδ2 T cells.

SUMMARY OF THE INVENTION

The current invention now provides for novel agents that can bind to Vγ9Vδ2 T cells. The agents provided are immunoglobulins. The immunoglobulins provided bind to a Vγ9Vδ2 T cell receptor. Surprisingly, it was found that the immunoglobulins provided by the current invention have a substantial sequence identity. Hence, in a first aspect of the invention, human Vγ9Vδ2 T cell receptor binding immunoglobulin molecules are provided, comprising a CDR1 region and a CDR 2 region, wherein the CDR1 region comprises an amino acid sequence with at least 40% sequence identity with the amino acid sequence of SEQ ID NO. 31 GRTFSNYAMG; and wherein the CDR2 region comprises an amino acid sequence with at least 60% sequence identity with the amino acid sequence of SEQ ID NO. 32 AISWSGGSTYYADSVKG; wherein preferably the immunoglobulin molecule is a single domain antibody.

Furthermore, such immunoglobulins comprise a CDR3 region, wherein the CDR3 region contributes to Vγ9Vδ2 T cell receptor binding and may have an effect on the action of the immunoglobulin molecule. This may, without being bound by theory, implicate the CDR3 sequence in the functionality of the immunoglobulin molecule, i.e. type of modulation such as blocking activation of Vγ9Vδ2 T cells, inducing activation of Vγ9Vδ2 T cells or neither blocking activation nor inducing activation of Vγ9Vδ2 T cells. The immunoglobulins of the invention are in particular for use in medical treatments and for use in assays involving Vγ9Vδ2 T cells.

Preferably, the immunoglobulin molecules according to the invention comprise a CDR3 region, wherein the CDR3 region comprises an amino acid sequence selected from the group consisting of amino acid sequences SEQ ID NO. 3, 6, 9, 11, 14, 17, 20, 22, 25, 27, 29, 30, 33, 35, 37, 40, 43, and 46. These CDR3 regions combined with the CDR1 and CDR2 sequences provided for binding and functions, as discussed in detail below.

FIGURES

FIG. 1: Alignment of the VHH sequences wherein the framework regions (1, 2, 3 and 4) are indicated as well as CDR1, CDR2 and CDR3. The code for each of the VHHs is indicated as well (i.e. 5C7 is the sequence of VHH 5C7).

Figure 2:
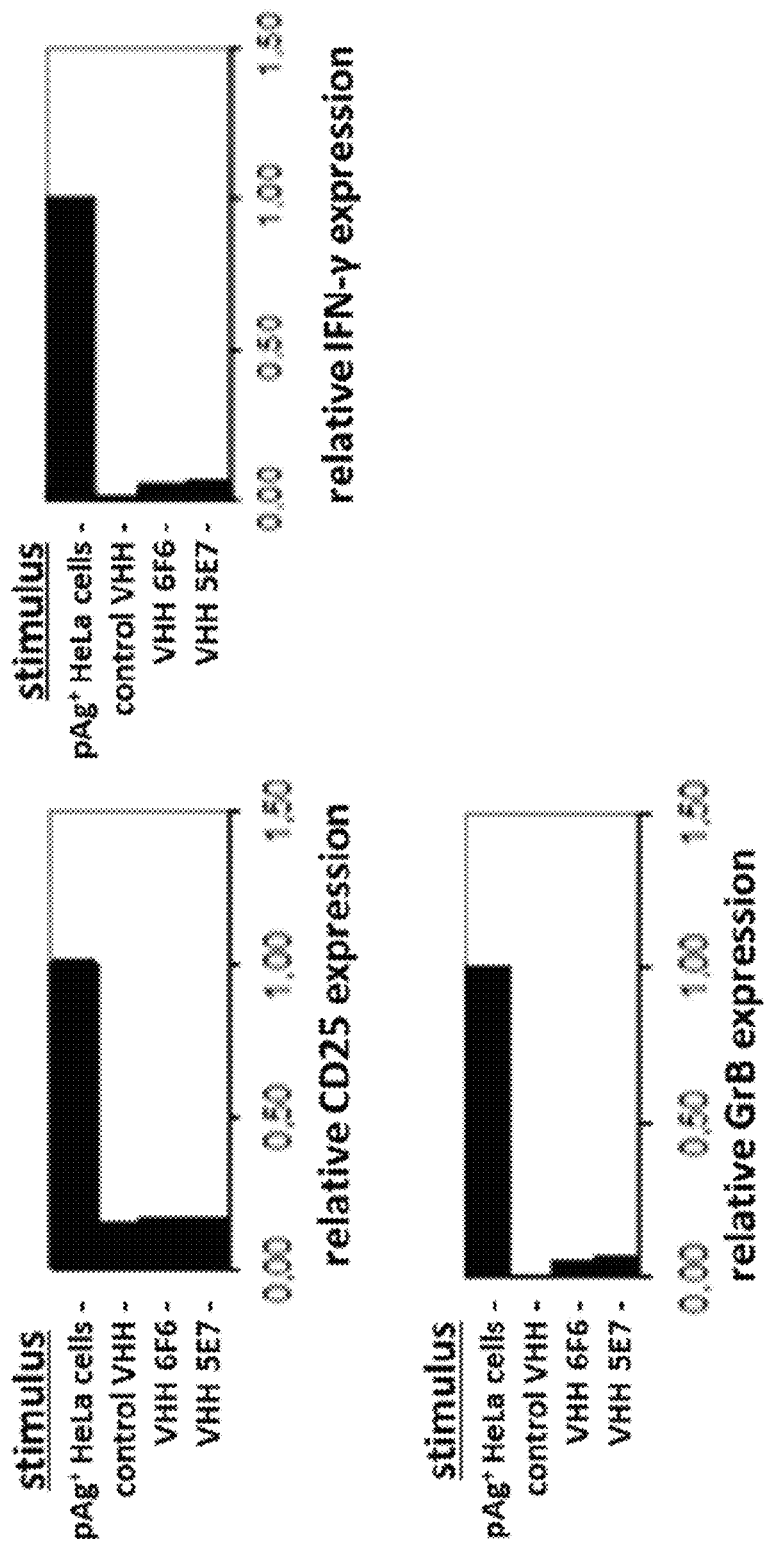

FIG. 2: VHH 5E7 and VHH 6F6 do not activate Vγ9Vδ2 T cells. Data indicate relative expression of the activation marker CD25, the pro-inflammatory cytokine IFN-γ, and the cytotoxic molecule granzyme B by healthy donor-derived Vγ9Vδ2 T cells in comparison with the positive control (phosphoantigen (pAg+) expressing HeLa cells)

Figure 3:
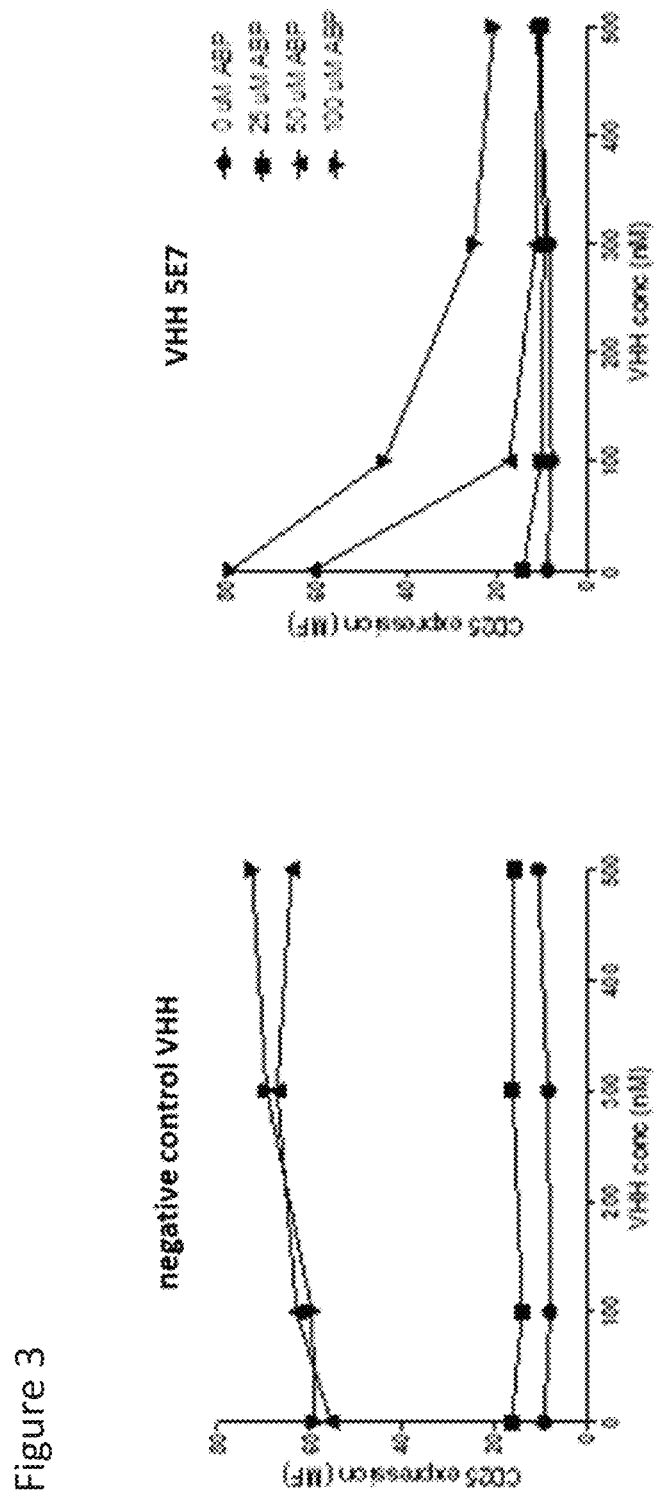

FIG. 3: VHH 5E7 neutralizes phosphoantigen induced activation of healthy donor-derived Vγ9Vδ2 T cells. A representative example demonstrates the dose dependent neutralization of phosphoAg-induced Vγ9Vδ2 T cell activation using VHH 5E7 while a non-specific VHH (negative control) cannot neutralize phosphoAg-induced Vγ9Vδ2 T cell activation. Vertical axis indicates activation of Vγ9Vδ2 T cells as assessed by CD25 expression, horizontal axis indicates different VHH concentrations. Vγ9Vδ2 T cell stimulations were performed using phosphoantigen expressing HeLa cells, generated by pretreating HeLa cells with increasing doses of the aminobisphosphonate pamidronate (which results in increasing levels of phosphoantigen expression by HeLa cells).

Figure 4:
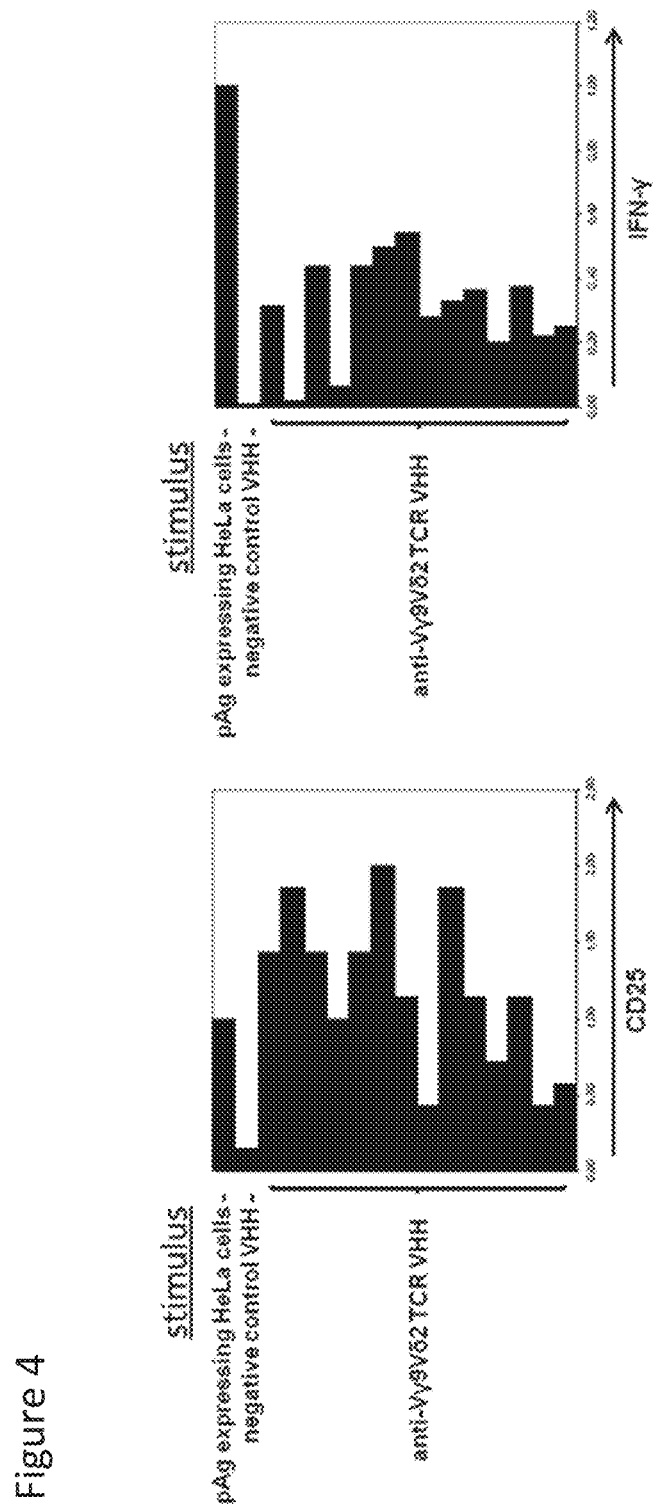

FIG. 4: Vγ9Vδ2 TCR specific VHH are capable of inducing activation and cytokine production in healthy donor-derived Vγ9Vδ2 T cells. Data indicate relative expression of the activation marker CD25 and the pro-inflammatory cytokine IFN-γ by healthy donor-derived Vγ9Vδ2 T cells in comparison with the positive control (phosphoantigen (pAg+) expressing HeLa cells; standardized to 1) and a negative control VHH. Each bar represents an individual Vγ9Vδ2 TCR specific VHH; individual VHHs differ with respect to their capacity to induce activation and cytokine production in Vγ9Vδ2 T cells.

Figure 5:
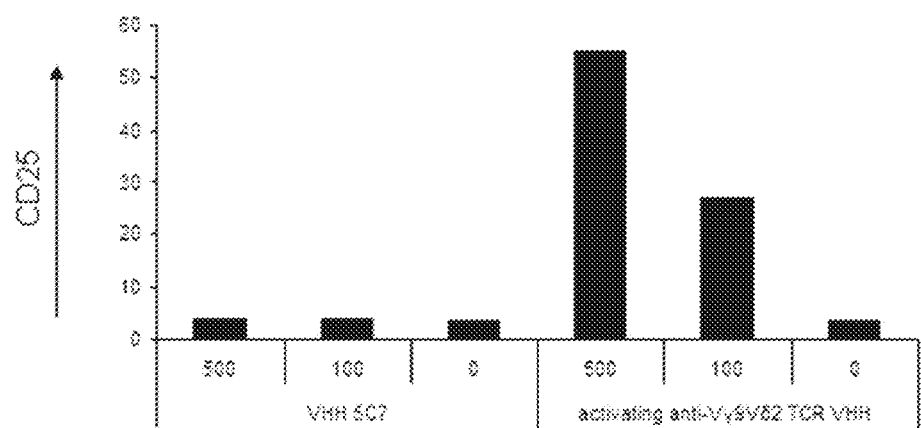

FIG. 5: Dose dependent activation of healthy donor-derived Vγ9Vδ2 T cells. Data indicate changes in CD25 expression (MFI) after 24 hr stimulation with increasing concentrations (10-100-500 nM) of either a non-activating anti-Vγ9Vδ2 TCR VHH or an activating anti-Vγ9Vδ2 TCR VHH.

Figure 6:
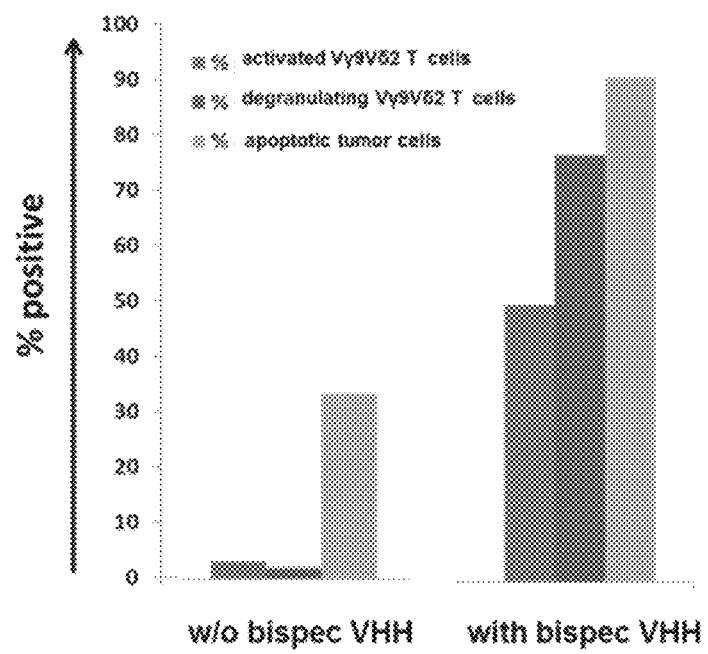

FIG. 6: Vγ9Vδ2 TCR specific VHH can promote tumour cell death when fused to a tumor antigen specific VHH as a bispecific molecule. Representative example of experiment in which Vγ9Vδ2 T cells were co-cultured overnight with the tumor cell line A431 in the presence (with) or absence (w/o) of a bispecfic nanobody construct consisting of a tumor-antigen specific VHH fused to an activating anti-Vγ9Vδ2 TCR VHH. Data indicate CD25 expression (activation), and CD107a expression (degranulation) of Vγ9Vδ2 T cells and 7AAD+ tumor cells (indicating tumor cell death).

Figure 7:
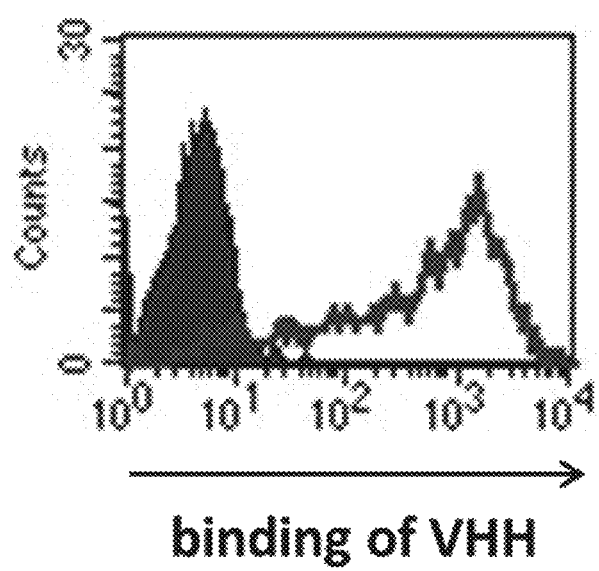

FIG. 7: T cell receptor Vγ9 and/or Vδ2 binding specificity as determined using flow-cytometry: Representative flow-cytometric histogram indicates binding of a Vγ9Vδ2 TCR specific VHH (open histogram) and a negative control VHH (filled histogram) to Vγ9Vδ2 TCR expressing cells.

Figure 8:
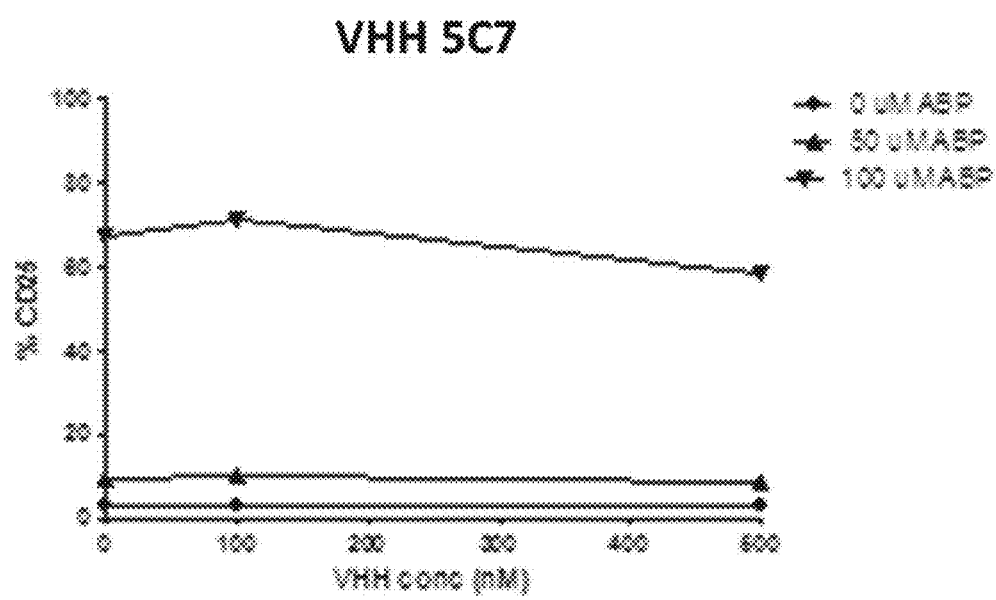

FIG. 8: Clone VHH 5C7 does not activate healthy donor-derived Vγ9Vδ2 T cells nor neutralize phosphoantigen induced activation of healthy donor-derived Vγ9Vδ2 T cells. Representative example demonstrating no inhibitory nor activating effect of VHH 5C7 on phosphoAg-induced Vγ9Vδ2 T cell activation. Vertical axis indicates activation of Vγ9Vδ2 T cells as assessed by CD25 expression, horizontal axis indicates different VHH concentrations. Vγ9Vδ2 T cell stimulations were performed using phosphoantigen expressing HeLa cells, generated by pretreating HeLa cells with increasing doses of the aminobisphosphonate pamidronate (which results in increasing levels of phosphoantigen expression by HeLa cells).

Figure 9:
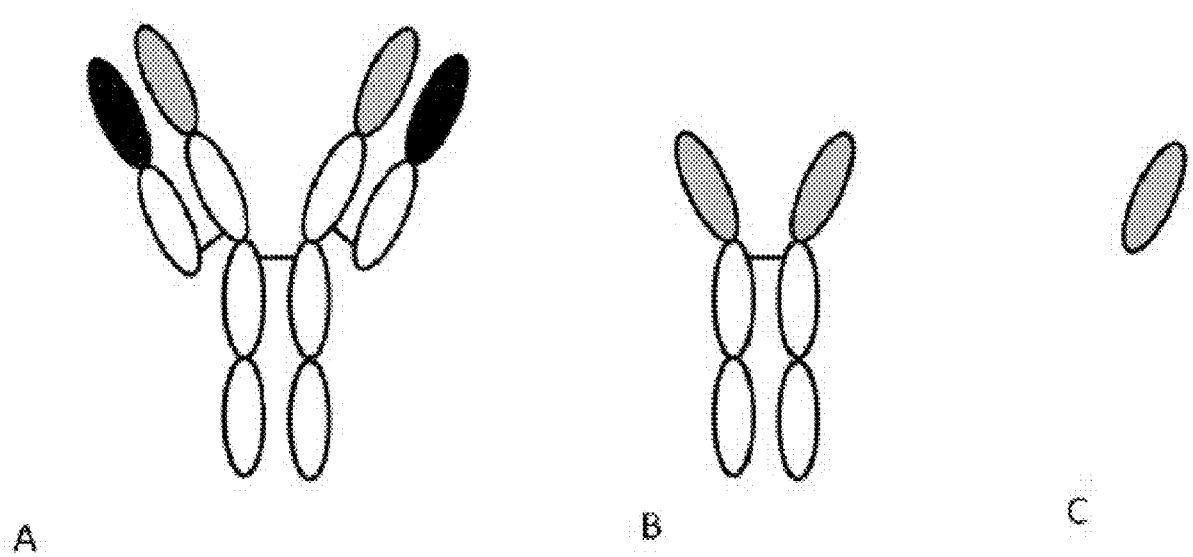

FIG. 9: Schematic of immunoglobulins.
A) A human antibody consisting of two heavy chains and two light chains; B) A single chain antibody (or heavy chain only antibody) consisting of two single chains (or two heavy chains) that can dimerize via disulphide bridges, wherein each chain contains a variable domain. Such a single chain antibody (or heavy chain only antibody) can be a llama antibody; C) A single domain antibody contains one variable antibody domain e.g. of a single chain antibody (or heavy chain only antibody). A single domain antibody can consist only of the binding region as depicted. The variable domain is indicated in grey, whereas the constant regions are indicated in white. The variable domain of the light chain is indicated in black.

Definitions

In the following description and examples a number of terms are used. In order to provide a clear and consistent understanding of the specifications and claims and clauses, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N. Y., 1989; Ausubel et al., Current Protocols in Molecular Biology, John Wiley & Sons, New York, 1987 and periodic updates; and the series Methods in Enzymology, Academic Press, San Diego.

In this document and in its claims and clauses, the verb "to comprise" and its conjugations is used in its non-limiting sense to mean that items following the word are included, but items not specifically mentioned are not excluded. It encompasses the verbs "consisting essentially of" as well as "consisting of".

As used herein, the singular forms "a," "an" and "the" include plural referents unless the context clearly dictates otherwise. For example, a method for isolating "a" DNA molecule, as used above, includes isolating a plurality of molecules (e.g. 10s, 100s, 1000s, 10s of thousands, 100s of thousands, millions, or more molecules).

Aligning and alignment: With the term "aligning" and "alignment" is meant the comparison of two or more amino acid sequences based on the presence of short or long stretches of identical or similar amino acids. Several methods for alignment of amino acid sequences are known in the art, as will be further explained below. With the term "aligning" and "alignment" is also meant the comparison of two or more nucleotide sequences based on the presence of short or long stretches of identical or similar nucleotides. Several methods for alignment of nucleotide sequences are known in the art, as will be further explained below.

"Expression of a gene" or "expression of a protein" refers to the process wherein a DNA region, which is operably linked to appropriate regulatory regions, particularly a promoter, is transcribed into an RNA, which is capable of being translated by machinery of the cell into a protein or peptide (or active peptide fragment) that is encoded by the nucleotide sequence or which is active itself (e.g. in posttranscriptional gene silencing or RNAi).

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two or more protein encoding regions, contiguous and in reading frame.

The term "genetic construct" means a DNA sequence comprising a region (transcribed region), which is transcribed into an RNA molecule (e.g. an mRNA) in a cell, operably linked to suitable regulatory regions (e.g. a promoter). A genetic construct may thus comprise several operably linked sequences, such as a promoter, a 5' leader sequence comprising e.g. sequences involved in translation initiation, a (protein) encoding region, splice donor and acceptor sites, intronic and exonic sequences, and a 3' non-translated sequence (also known as 3' untranslated sequence or 3'UTR) comprising e.g. transcription termination sequence sites.

"sequence identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER; Gribskov, M. and Devereux, J., eds., M Stockton Press, New York, 1991). While a number of methods exist to measure identity between two polynucleotide or polypeptide sequences, the term "identity" is well known to skilled artisans (Carillo, H., and Lipton, D., SIAM J. Applied Math (1988) 48:1073). Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., SIAM J. Applied Math (1988) 48:1073. Methods to determine identity and similarity are codified in computer programs. Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al., J. Molec. Biol. (1990) 215:403).

As an illustration, by an amino acid sequence with at least, for example, 70% "sequence identity" to a reference amino acid sequence of SEQ ID NO: 31 it is intended that the amino acid sequence is identical to the reference sequence except that the polypeptide sequence may include up to 3 amino acid alterations per each of the 10 amino acids of the reference amino acid of SEQ ID NO: 31. Hence, the percentage of identity of an amino acid sequence to a reference amino acid sequence is to be calculated over the full length of the reference amino acid sequence. In other words, to obtain an amino acid sequence comprising at least 70% identical to a reference amino acid sequence, up to 30% of the amino acid residues in the reference sequence may be deleted or substituted with another amino acid, or a number of amino acids up to 30% of the total amino acid residues in the reference sequence may be inserted into the reference sequence. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

A "nucleic acid" or "nucleic acid sequence" according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982), which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogeneous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

As used herein, the term "cancer" refers to or describes the physiological condition in mammals that is typically characterized by unregulated cell growth. Examples of cancer include, but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, skin cancer, blood cancer, leukemia, melanoma, head and neck cancer, and brain cancer. As used herein, "cancer" is also referred to as malignant neoplasm.

The terms "amino acid sequence" or "protein" or "peptide" refer to molecules consisting of a chain of amino acids, without reference to a specific mode of action, size, 3 dimensional structure or origin. A "fragment" or "portion" of thereof may thus still be referred to as an "amino acid sequence" or "protein" or "peptide". An "isolated amino acid sequence" is used to refer to an amino acid sequence which is no longer in its original natural environment, for example in vitro or in a recombinant bacterial or human host cell.

"T cells", or "T lymphocytes", belong to a group of white blood cells named lymphocytes, which play a role in cell-mediated immunity. T cells originate from hematopoietic stem cells in the bone marrow, mature in the thymus (that is where the T is derived from), and gain their full function in peripheral lymphoid tissues. During T-cell development, $CD4^-CD8^-$ T-cells (negative for both the CD4 and CD8 co-receptor) are committed either to an $\alpha\beta$ or $\gamma\delta$ fate as a result of an initial $\beta$ or $\delta$ TCR gene rearrangement. Cells that undergo early $\beta$ chain rearrangement express a pre-TCR structure composed of a complete $\beta$ chain and a pre-TCR$\alpha$ chain on the cell surface. Such cells switch to a $CD4^+CD8^+$ state, rearrange the TCR$\alpha$ chain locus, and express a mature $\alpha\beta$TCR on the surface. $CD4^-CD8^-$ T cells that successfully complete the $\gamma$ gene rearrangement before the $\beta$ gene rearrangement express a functional $\gamma\theta$TCR and remain $CD4^-CD8^-$. (Claudio Tripodo et al. Gamma delta T cell lymphomas Nature Reviews Clinical Oncology 6, 707-717 (December 2009). The T cell receptor associates with the CD3 protein complex. Mature T cells, i.e. expressing a $\alpha\beta$TCR or a $\gamma\delta$TCR, express the T cell receptor complex on the cell surface. The $\gamma\delta$T-cells, which constitute about 1-5% of the total population of T cells in human peripheral blood, can be divided in further subpopulations. A subpopulation of $\gamma\delta$T-cells constitutes V$\gamma$9V$\delta$2 T-cells, which express a V$\gamma$9V$\delta$2 TCR. Within the extracellular domain of a T cell receptor complementarity determining regions (CDR1, CDR2, CDR3) are located. These regions are in general the most variable domains and contribute significantly to the diversity among TCRs. CDR regions are composed during the development of a T-cell where so-called Variable-(V), Diversity-(D), and Joining-(J)-gene segments are randomly combined to generate diverse TCRs.

"V$\gamma$9V$\delta$2 T-cells" are cells that may be functionally defined in that they are specifically and rapidly activated by a set of non-peptidic phosphorylated isoprenoid precursors, collectively named phosphoantigens. Phosphoantigens are produced by virtually all living cells. The most common phosphoantigen found in animal and human cells (including cancer cells) is isopentenyl pyrophosphate (IPP) and its isomer dimethylallyl pyrophosphate (DMAPP). IPP is a metabolite from the mevalonate pathway. (E)-4-Hydroxy-3-methyl-but-2-enyl pyrophosphate (HMBPP or HMB-PP) is an intermediate of the non-mevalonate pathway of isoprenoid biosynthesis. HMBPP is an essential metabolite in most pathogenic bacteria, including *Mycobacterium tuberculosis*, as well as in parasitic protozoans, such as *Plasmodium* (causing malaria) and *Toxoplasma gondii*. Activation of Vγ9Vδ2 T-cells comprises clonal expansion, cytoxic activity and expression of cytokines. "Vγ9Vδ2 T-cells" are also defined by expression of the Vγ9Vδ2 T-cell receptor. For example, cells may be selected using an antibody specific for the Vγ9Vδ2 T-cell receptor such as described below. These selected cells have undergone rearrangement of the γ and δ gene and encode a Vγ9 T-cell receptor chain and a Vδ2 T-cell receptor chain. From such selected cells, the nucleic acid (or amino acid) sequence corresponding to the Vγ9 T-cell receptor chain and the Vδ2 T-cell receptor chain may be determined.

The person skilled in the art is well capable of selecting and/or identifying cell populations characterized by expression of an antigen or receptor on the surface of the cell such as described throughout herein. It is understood that with regard to expression on the surface of cells, such as CD3, CD4, CD8, CD25, CD69, γδTCR and Vγ9Vδ2 TCR, this is typically done in a population of cells of which a portion of cells has a much higher level of expression of the antigen or receptor when compared to cells having a lower level of expression. Hence, the terms positive or negative are to be understood as being relative, i.e. positive cells have a much higher expression level as compared to cells being negative. Cells being negative in this sense may thus still have an expression level which may be detected. Expression on the surface of cells may be analysed using Fluorescence Activated Cell Sorting (FACS), and many specific antibodies are commercially available, e.g. such as for CD3, CD4, CD8, CD25, CD69, γδTCR, Vγ9 TCR chain and Vδ2 TCR chain, that are suitable for such FACS analysis, such as described in the examples and as available. Such specific antibodies are immunoglobulins that bind with their respective antigen or receptor. Vγ9Vδ2 T-cells can hence also be defined and selected as being positive for Vγ9Vδ2 TCR in FACS. Antibodies suitable for FACS or similar separation techniques (such as e.g. antibodies conjugated to magnetic beads) are widely available. Conditions are selected, such as provided by the antibody manufacturer that allows the selection of negative and/or positive cells. Examples of antibodies that may be suitable for selection of Vγ9Vδ2 T cells, or engineered Vγ9Vδ2 T-cells such as available from BD Pharmingen (BD, 1 Becton Drive, Franklin Lakes, N.J. USA) are Vγ9-PE (clone B3, #555733), V82-FITC (clone B6, #555738), γδTCR-APC (clone B1, #555718) or such as available from Beckman Coulter is pan-γδTCR-PE (clone IMMU510, #IM1418U). Examples of antibodies that may be suitable for detecting CD25 and CD69 are CD25-PE (clone M-A251, #555432) and CD69-FITC (clone L78, #347823) available from BD Pharmingen.

DETAILED DESCRIPTION OF THE INVENTION

In a first aspect of the invention, a human Vγ9Vδ2 T cell receptor binding immunoglobulin molecule is provided, comprising a CDR1 region and a CDR 2 region, wherein the CDR1 region comprises an amino acid sequence with at least 40% sequence identity with the amino acid sequence of SEQ ID NO. 31 GRTFSNYAMG;
wherein the CDR2 region comprises an amino acid sequence with at least 60% sequence identity with the amino acid sequence of SEQ ID NO. 32 AISWSGGSTYYADSVKG;
wherein preferably the immunoglobulin molecule is a single domain antibody.

A human Vγ9Vδ2 T cell receptor binding immunoglobulin molecule according to the invention, is an immunoglobulin molecule that binds e.g. to a Vγ9Vδ2 T cell receptor such as defined by the amino acid sequences of the Vγ9 and Vδ2T cell receptor chains as listed in SEQ ID NO. 71 and 72. Binding to such a T cell receptor can be detected e.g. via FACS analysis, such as described in the example section. For example, cells expressing a Vγ9Vδ2 T cell receptor, e.g. SEQ ID NO. 71 and 72, are contacted with either a control immunoglobulin molecule or an immunoglobulin molecule binding to a Vγ9Vδ2 T cell receptor. Alternatively, Vγ9Vδ2 T cells derived from a healthy human donor as described in the examples can be contacted with either a control immunoglobulin molecule or an immunoglobulin molecule binding to a Vγ9Vδ2 T cell receptor. The amount of immunoglobulin bound to the cell is increased when the specific immunoglobulin molecule is compared with a control immunoglobulin molecule that does not bind to a Vγ9Vδ2 T cell receptor (see for example FIG. 7). A human Vγ9Vδ2 T cell receptor binding immunoglobulin molecule according to the invention can be defined e.g. as being an immunoglobulin that results in a minimal 2-fold increase in mean-fluorescence intensity (MFI), relative to a control immunoglobulin, as determined by flow cytometry. The MFI is the mean of the fluorescence intensity in the fluorescence channel that is chosen (FITC, PE, PerCP, etc.). As a negative control antibody a single domain antibody (or VHH, nanobody) against azo-dye reactive red 6 (RR6) can be used (Spinelli S et al, Biochemistry 2000; 39:1217-1222). Hence, the skilled person is well capable of selecting appropriate conditions to determine binding of an immunoglobulin molecule with the Vγ9Vδ2 T cell receptor. Immunoglobulin binding can be expressed in terms of specificity and affinity. The specificity determines which antigen or epitope thereof is bound by the immunoglobulin molecule.

An "immunoglobulin molecule" (abbreviated as "Ig") as used herein is well-known in the art and comprises the term "antibody". The term "immunoglobulin" as used herein refers to any polypeptide comprising an antigen-binding site with complementarity determining regions (CDR). The term includes, but is not limited to antibodies, monoclonal antibodies, monospecific antibodies, multispecific antibodies, humanized antibodies, chimeric antibodies, human antibodies, single chain antibodies, heavy chain only antibodies, llama antibodies, single domain antibodies and nanobodies (e.g. VHH). The term "immunoglobulin molecule" may also include immunoglobulin fragments such Fab, F(ab')2, Fv, scFv, Fd, dAb, and other antibody fragments or other constructs comprising CDRs that retain antigen-binding function. Typically, such fragments comprise an antigen-binding domain. The immunoglobulin molecules or fragments thereof may be any of the known antibody isotypes and their conformations, for example, IgA, such as IgA1 or IgA2, IgD, IgE, IgG, such as IgG1, IgG2a, IgG2b, IgG3, IgG4, or IgM class, or may constitute mixtures thereof in any combination, such as a mixture of antibodies from the IgG1 and IgG2a class.

Immunoglobulins are immune system-related proteins. Human antibodies consist of four polypeptides—two heavy chains and two light chains joined to form a "Y"-shaped molecule (see FIG. 9A). The amino acid sequence in the tips of the "Y" varies greatly among different antibodies. Each of the tips has a specificity for binding antigen. The variable region of human antibodies includes the ends of the light and heavy chains, i.e. the variable domains of the light and heavy chains. The constant region determines the mechanism used to e.g. activate the immune system.

Antibodies are divided into five major classes, IgM, IgG, IgA, IgD, and IgE, based on their heavy chain constant region structure and immune function. Also subclasses of the heavy chain are known. For example, IgG heavy chains in humans can be any of the IgG1, IgG2, IgG3 and IgG4 subclasses.

Each chain, i.e. immunoglobulin molecule, has a variable domain. The variable domain of immunoglobulin molecules is subdivided into hypervariable (HV) and framework (FR) regions. HV regions have a high ratio of different amino acids in a given position, relative to the most common amino acid in that position. The hypervariability regions are referred to as complementarity determining regions (CDR). Immunoglobulin molecules have three complementarity determining regions (CDR1, CDR2 and CDR3). Four framework regions, with much less variable amino acids sequences, separate the CDR regions. The CDR regions can direct binding to the antigen, such as a Vγ9Vδ2 T cell receptor (see for example FIG. 1, wherein the framework regions and CDR regions are indicated of the selected VHHs). The framework regions form a beta-sheet structure which serves as a scaffold to position the CDR regions to contact the antigen.

Llama antibodies consist of two heavy chains (see FIG. 9B). Each of the heavy chains is an immunoglobulin molecule with a single variable domain. Such an antibody is referred to as a single chain antibody, i.e. it comprises one type of chain. Such an antibody can also be referred to as a heavy chain only antibody.

A single domain antibody is an immunoglobulin molecule containing a single monomeric variable domain (see FIG. 9C). Single domain antibodies thus contain a single CDR1, a single CDR2 and a single CDR3. A single domain antibody can be derived from a single chain antibody (or heavy chain only antibody). Like a whole antibody, a single domain antibody is able to bind selectively to a specific antigen. Single domain antibodies may contain only the variable domain of an immunoglobulin chain having CDR1, CDR2 and CDR3 and framework regions, such antibodies can also be referred to as VHHs or nanobodies. With a molecular weight of only about 12-15 kDa, nanobodies are much smaller than common antibodies (150-160 kDa) which are composed of two heavy chains and two light chains.

CDR1, CDR2 and CDR3 sequences may be exchanged between species. For example, from a llama immunoglobulin molecule, CDR sequences may be selected and exchanged with CDR sequences in a human immunoglobulin molecule, to obtain a human immunoglobulin molecule having the specificity that is derived from the llama CDR sequences. This may be advantageous as a human sequence may be less immunogenic to humans as compared to the original llama framework sequence. Such an exchange of CDR sequences is known as humanization. Hence, the immunoglobulin molecules, single chain antibodies and single domain antibodies according to the invention may have human derived immunoglobulin sequences or llama derived immunoglobulin sequences and have the CDR1, CDR2 and CDR3 sequences replaced with the CDR sequences according to the invention in order to provide for human Vγ9Vδ2 T cell receptor binding. For example, a single chain human antibody may comprise a sequence corresponding to the human heavy chain sequence but has been mutated, e.g. having the CH1 domain deleted, such that a llama-like single chain antibody is formed (see e.g. FIG. 9B), and has the CDR regions of said human heavy chain sequence replaced by the CDR sequences according to the invention. A human immunoglobulin, a human single chain antibody or a human single domain antibody hence refers to the origin of framework and/or constant regions and not to the origin of the CDR1, CDR2 and CDR3 regions of the invention.

As described in the example section, human Vγ9Vδ2 T cell receptor binding immunoglobulin molecules were selected by using a strategy involving immunizing Llama glamas with human donor-derived Vγ9Vδ2 T cells and phage display. The VHH sequences that were selected were sequenced and are listed in table 3 and depicted in FIG. 1. The CDR1, CDR2 and CDR3 regions of the selected VHHs are listed below in table 1. Each of the CDRs is also listed in table 3 with the corresponding SEQ ID NO.

Table 1. Of the 20 VHHs that were selected the CDR1, CDR2 and CDR3 sequences are listed. The Ref. CDR1 and CDR2 are listed above (corresponding to SEQ ID NO. 31 and SEQ ID NO. 32 respectively), and the sequence identify (%) of each CDR1 and CDR2 region with the respective Ref. CDR1 and CDR2 is listed as well.

| Nr | Ref | CDR1 | % | CDR2 | % | CDR3 |
|---|---|---|---|---|---|---|
| | | GRTFSNYAMG | | AISWSGGSTYYADSVKG | | |
| 1 | 5C7 | GRTFSRYTMG | 80 | AISWSGGRTNFAGSVKG | 71 | DWLPVPGRESYDY |
| 2 | 5E3 | GRTFSSYAMG | 90 | AISWSGGTTYYADSVKG | 94 | SLDCSGPGCHTAEYDY |
| 3 | 6H1 | GRTFSEYAMG | 90 | AISWTGSKTYYADSVKG | 82 | SSDCSGPGCHTEEYDY |
| 4 | 5G3 | GRTFSSYAMG | 90 | AVSWSGGSTYYADSVKG | 94 | SQDCSGPGCYTNEYDS |
| 5 | 5C1 | GSIFSNYAMA | 70 | AVSWSGGRTYYADSVKG | 88 | SLSCSGPGCSLEEYDY |
| 6 | 5D3 | GRPFSNYAMG | 90 | VISWSGGSTYYADSVKG | 94 | QFSGASTVVAGTALDYDY |
| 7 | 6E3 | GRPFSNYGMG | 90 | GISWSGGSTDYADSVKG | 88 | VFSGAETAYYPSDDYDY |
| 8 | 6H4 | GRPFSNYGMG | 90 | GISWSGGSTDYADSVKG | 88 | VFSGAETAYYPSDDYDY |

-continued

| Nr | Ref | CDR1 | % | CDR2 | % | CDR3 |
|---|---|---|---|---|---|---|
| 9 | 6C1 | GRPFSNYGMG | 90 | GISWSGGSTDYADSVKG | 94 | VFSGAETAYYPSDDYDY |
| 10 | 6H3 | GRPFSNYGMG | 90 | GITWSGGSTHYADLVKG | 76 | VFSGAETAYYPSTEYDY |
| 11 | 6G3 | GRPFNNYGMG | 70 | GISWSGGSTYYADSVKG | 94 | VFSGAETAQYPSYDYDY |
| 12 | 6F6 | GRPFSNYAMG | 90 | AVTWSGGSTYYADSVKG | 88 | QFNGAENIVPATTTPTSYDY |
| 13 | 5C8 | GRPFSNYAMG | 90 | AISWSGGSTSYADSVKG | 94 | QFSGADYGFGRLGIRGYEYDY |
| 14 | 5E7 | GRPFSNYAMG | 90 | AISWSGGSTSYADSVKG | 94 | QFSGADYGFGRLGIQGYEYDY |
| 15 | 5F5 | GRTFSNYAMG | 100 | AISWSGGSTYYADSVKG | 100 | MFSGSESQLVVVITNLYEYDY |
| 16 | 6A1 | GRTFSNYAMG | 100 | TISWSGGSTYYADSVKG | 94 | AFSGSDYANTKKEVEYDY |
| 17 | 5D7 | GRTFSNYAMG | 100 | AISWSGGMTDHADSVKG | 82 | AFAGDIPYGSSWYGDPTTYDY |
| 18 | 5B11 | GRTSSTFSMA | 50 | AINWSGGSTRYADSVSD | 76 | RRGGIYYSTQNDYDY |
| 19 | 6C4 | VRTFSDYRMG | 70 | TISWSGGLTYYADSVKG | 94 | GGGYAGGTYYHPEE |
| 20 | 6E4 | GFTFDDYCIA | 40 | CITTSDGSTYYADSVKG | 76 | YFGYGCYGGAQDYRAMDY |

The Ref. CDR1 and CDR2 are listed above (corresponding to SEQ ID NO. 31 and SEQ ID NO. 32 respectively), and the sequence identify (%) of each CDR1 and CDR2 region with the respective Ref. CDR1 and CDR2 is listed as well.

The immunoglobulins that were selected by the inventors to bind the human Vγ9Vδ2 T cell receptor surprisingly had a substantial sequence identity with regard to CDR1 and CDR2. Without being bound by theory, such CDR1 and CDR2 sequences substantially contribute to the binding of the Vγ9Vδ2 T cell receptor. More variability was found for the CDR3 region, which, without being bound by theory, may implicate the CDR3 sequence in the functionality of the immunoglobulin molecule, i.e. type of modulation such as blocking activation of Vγ9Vδ2 T cells, inducing activation of Vγ9Vδ2 T cells or neither blocking activation nor inducing activation of Vγ9Vδ2 T cells. Hence, the immunoglobulin molecule comprises a CDR1 region and a CDR2 region, wherein the CDR1 region comprises an amino acid sequence with at least 40% sequence identity with the amino acid sequence of SEQ ID NO. 31 GRTFSNYAMG, and wherein the CDR2 region comprises an amino acid sequence with at least 60% sequence identity with the amino acid sequence of SEQ ID NO. 32 AISWSGGSTYYADSVKG. Preferably the CDR2 region comprises an amino acid sequence with at least 70% sequence identity with the amino acid sequence of SEQ ID NO. 32.

Preferably, the immunoglobulin molecule is a single chain antibody. As said, the immunoglobulins are derived from llama. Lllamas produce antibodies with a single heavy chain that dimerizes via disulphide bridges, i.e. a llama antibody has two single variable domains from two chains (see FIG. 9B).

In one embodiment, the CDR2 region comprises an amino acid sequence with at least 60% sequence identity with SEQ ID NO. 32 AISWSGGSTYYADSVKG, wherein the said amino acid sequence has a T at position 9, an A at position 12, and a V at position 15. When the sequences of the selected CDR2 regions are compared, the amino acids at these positions do not show variation. Hence, without being bound by theory, these positions appear to be of importance to binding the Vγ9Vδ2 T cell receptor. It is understood that the position referred to relates to the position in the reference sequence and does not refer to the position in the immunoglobulin molecule as a whole. Hence, the CDR2 region has identical amino acids to SEQ ID NO. 32 at the specified position.

As described in the example section, the CDR1, CDR2 and CDR3 regions were selected from llama antibodies. Hence, a single chain antibody according to the invention may comprise immunoglobulin molecule sequences that are derived from the llama. It is understood that in such a llama single chain antibody, the original CDR sequences are replaced by replacement CDR sequences, e.g. such as listed in table 1, to arrive at a llama single chain having the specificity of the replacement CDR sequences. Similarly, the same may be done with a human heavy chain sequences. The human single chain antibody than having the specificity being governed by the replacement CDR sequences. Transferring CDR1, CDR2 and CDR3 regions to other frameworks, e.g. to other species such as human frameworks is well known in the art.

In one embodiment, the single chain antibody is a single domain antibody. Single chain antibodies comprise framework regions. Hence, a human single domain antibody may have human framework regions, e.g. derived from either a human heavy and/or human light chain sequence and CDR1, CDR2 and CDR3 sequences according to the invention. A llama single domain antibody has llama framework regions.

In one embodiment, one or more of the framework regions are selected from the group of amino acid sequences of SEQ ID NO. 67-70. These framework regions are the framework regions from one of the VHH clones that was isolated. As can be observed, the framework regions from the 20 isolated clones do not vary substantially.

In one embodiment, the immunoglobulin molecule, the single chain antibody or the single domain antibody comprises a CDR3 region, wherein the CDR3 region comprises an amino acid sequence selected from the group consisting of amino acid sequences SEQ ID NO. 3, 6, 9, 11, 14, 17, 20, 22, 25, 27, 29, 30, 33, 35, 37, 40, 43, and 46. These CDR3 regions combined with the CDR1 and CDR2 sequences provided for binding and function, as discussed below.

In one embodiment, the immunoglobulin molecule, the single chain antibody or the single domain antibody has the combinations of the amino acid sequences of the CDR1, CDR2 and CDR3 regions from the antibodies such as listed in table 1. In one embodiment, the immunoglobulin molecule, the single chain antibody or the single domain antibody comprises an amino acid sequence selected from the group of amino acid sequences consisting of SEQ ID NO. 47-66.

In one embodiment, an immunoglobulin molecule according to the invention as disclosed above is provided for use in a medical treatment. It is understood that a human Vγ9Vδ2 T cell receptor binding immunoglobulin molecule when it binds a human Vγ9Vδ2 T cell in vivo, e.g. in a medical treatment, that it may not be desirable that the immunoglobulin molecule is a fully functional immunoglobulin molecule as upon binding to human Vγ9Vδ2 T cells it may trigger an immune response directed against the human Vγ9Vδ2 T cells. Hence, in such a scenario, immunoglobulin molecules that do not have functional constant regions, i.e. inactivated or deleted, are preferred such as e.g. in nanobodies and VHHs. This may be in particular useful when the action of the human Vγ9Vδ2 T cells is required in vivo.

In one embodiment, a nucleotide sequence is provided that encodes an immunoglobulin molecule according to the invention. The sequences as disclosed herein relate to amino acid sequences. Hence, the skilled person is well capable of providing for a nucleotide sequence encoding an amino acid sequence, as it only requires to use a codon table to convert amino acid sequence into nucleotide sequence. Such nucleotide sequence may be used to operably link it to promoter sequences, polyA signals etc., to provide for a genetic construct with which the antibody may be expressed. Such a genetic construct comprising the nucleotide sequence may be comprised in a host cell.

In one embodiment, a method is provided for preparing an immunoglobulin molecule according to the invention comprising:
culturing a host cell according to the invention comprising a nucleotide sequence that encodes an immunoglobulin molecule according to the invention;
allowing the host cell to express the immunoglobulin;
obtaining the immunoglobulin.

Furthermore, the invention also provides for a human Vγ9Vδ2 T cell receptor binding immunoglobulin molecule, wherein the immunoglobulin molecule is an immunoglobulin molecule that blocks activation of human Vγ9Vδ2 T cells. Blocking activation of human Vγ9Vδ2 T cells is advantageous in conditions and/or treatments wherein activation of human Vγ9Vδ2 T cells is undesirable.

Vγ9Vδ2 T cells can be strongly and specifically activated by small nonpeptidic phosphorylated intermediates, referred to as phosphoantigens (pAg) from the mammalian mevalonate pathway or the microbial deoxyxylulose-phosphate pathways. Phosphoantigens can then be specifically recognized (resulting in activation) by Vγ9Vδ2 T cell through interaction between pAg and membrane bound butyrophilin3A1/CD277 molecules. Vγ9Vδ2 T cell receptor binding immunoglobulin molecules, as shown in the examples, can block phosphoantigen induced activation of Vγ9Vδ2 T cells.

Preferably, the human Vγ9Vδ2 T cell receptor binding immunoglobulin molecule, wherein the immunoglobulin molecule is an immunoglobulin molecule that blocks activation of human Vγ9Vδ2 T cells, is a human Vγ9Vδ2 T cell receptor binding immunoglobulin molecule, comprising a CDR1 region and a CDR 2 region, wherein the CDR1 region comprises an amino acid sequence with at least 40% sequence identity with the amino acid sequence of SEQ ID NO. 31 GRTFSNYAMG; and wherein the CDR2 region comprises an amino acid sequence with at least 60% sequence identity with the amino acid sequence of SEQ ID NO. 32 AISWSGGSTYYADSVKG; and wherein preferably the immunoglobulin molecule is a single chain antibody. In one embodiment, the CDR2 region of said immunoglobulin molecule comprises an amino acid sequence with at least 60% sequence identity with SEQ ID NO. 2 AISWSGG-STYYADSVKG, wherein the said amino acid sequence has a T at position 9, an A at position 12, and a V at position 15. In a further embodiment, the immunoglobulin molecule is a single domain antibody, preferably wherein the single domain antibody is derived from a llama single chain antibody or a human single chain antibody. In a further embodiment, the immunoglobulin molecule is a single chain antibody or a single domain antibody. In further embodiments, the immunoglobulin molecule or the single chain antibody or the single domain antibody, comprises one or more of the framework regions selected from the group of amino acid sequences of SEQ ID NO. 67-70.

In one embodiment, the said human Vγ9Vδ2 T cell receptor binding immunoglobulin molecule that blocks activation of human Vγ9Vδ2 T cells is for use in a medical treatment. In a further embodiment, said immunoglobulin molecule is for use in a medical treatment, wherein the medical treatment comprising the use of inhibitors of the mevalonate pathway or wherein the medical treatment comprises the treatment of cancer. In another further embodiment said immunoglobulin molecule is for use in a medical treatment wherein the medical treatment comprises the treatment of an infectious disease.

Inhibitors of the mevalonate pathway that act downstream of pAg production, that include commonly clinically prescribed aminobisphosphonates such as pamidronate, alendronate, risedronate, ibandronate and zoledronate. Another class of compounds includes alkylamines such as isobutylamine, isoamylamine, and n-butylamine. Such compounds can be used for the treatment of Paget's disease, osteoporosis, hypercalcemia, and prevention of skeletal events in case of malignant bone metastases. This results in the intracellular accumulation of the endogenous pAg isopentenyl-pyrophosphate (IPP) and the subsequent selective activation and expansion of Vγ9Vδ2 T cells. Aminobisphosphonate administration is frequently accompanied by an acute febrile response due to this selective activation of Vγ9Vδ2 T cells. This acute phase response has a peak onset of 1 day and a median duration of 3 days and mostly consists of fever, chills, flushes, acute musculoskeletal symptoms, pain, generalized discomfort and local complaints involving the back, neck, chest or shoulders, nausea, vomiting, and diarrhea. Hence, in a medical treatment, said human Vγ9Vδ2 T cell receptor binding immunoglobulin molecules that block activation of human Vγ9Vδ2 T cells can prevent the acute phase response induced by e.g. aminobisphosphonate administration in patients with Paget's disease, osteoporosis, bone metastases, and hypercalcemia. Furthermore, such immunoglobulin molecules may also be advantageous in the medical treatment of excessive activation of Vγ9Vδ2 T cells in vivo, which can occur for example during an infection where Vγ9Vδ2 T cells are overstimulated or chronically stimulated or in certain cancerous conditions where chronic overactivity of the mevalonate pathway in tumour cells can result in Vγ9Vδ2 T cell exhaustion. Such (over)stimulation can be measured in patients for example by measuring an increase in Vγ9Vδ2 T cells as compared to baseline levels, or by measuring supranormal levels of Vγ9Vδ2 T cells, e.g. more than 5% of the T cells are Vγ9Vδ2 T cells, combined with an upregulation of surface markers such as CD69 (early activation marker) or CD25 (late activation marker) on Vγ9Vδ2 T cells. It is understood that due to migration of the Vγ9Vδ2 T cells out of the blood to tissues, measuring supranormal levels of Vγ9Vδ2 T cells is not a requirement. On the other hand, in chronic overstimulation, Vγ9Vδ2 T cells may be less well activated, and that can be a sign of overstimulation as well. Cytokine production (IFN-gamma, TNF-alpha) and cytotoxic granule content can also be measured intracellularly by flow cytometry.

In a preferred embodiment, the said human Vγ9Vδ2 T cell receptor binding immunoglobulin molecule that blocks activation of human Vγ9Vδ2 T cells, is an immunoglobulin molecule comprising a CDR3 region, wherein the CDR3 region comprises an amino acid sequence selected from the group consisting of amino acid sequences SEQ ID NO. 27 and 30.

In one embodiment, the said human Vγ9Vδ2 T cell receptor binding immunoglobulin molecule that blocks activation of human Vγ9Vδ2 T cells, is used for blocking activation of human Vγ9Vδ2 T cells. According to this embodiment, said immunoglobulin molecule (which includes the single chain antibody or single domain antibody), is used in assays, e.g. such as described in the examples, to block activation.

The invention also provides an immunoglobulin molecule that activates human Vγ9Vδ2 T cells, that is a human Vγ9Vδ2 T cell receptor binding immunoglobulin molecule, comprising a CDR1 region and a CDR2 region, wherein the CDR1 region comprises an amino acid sequence with at least 40% sequence identity with the amino acid sequence of SEQ ID NO. 31 GRTFSNYAMG; and wherein the CDR2 region comprises an amino acid sequence with at least 60% sequence identity with the amino acid sequence of SEQ ID NO. 32 AISWSGGSTYYADSVKG; and wherein preferably the immunoglobulin molecule is a single chain antibody. In one embodiment, the CDR2 region comprises an amino acid sequence with at least 60% sequence identity with SEQ ID NO. 2 AISWSGGSTYYADSVKG, wherein the said amino acid sequence has a T at position 9, an A at position 12, and a V at position 15. In a further embodiment, the immunoglobulin molecule is a single domain antibody, preferably wherein the single domain antibody is a llama single chain antibody or a human single chain antibody. In a further embodiment, the single chain antibody is a single domain antibody. In further embodiments, the immunoglobulin molecule or the single chain antibody or the single domain antibody, comprises one or more of the framework regions selected from the group of amino acid sequences of SEQ ID NO. 67-70.

Preferably, said immunoglobulin molecules that activate human Vγ9Vδ2 T cells comprises a CDR3 region, wherein the CDR3 region comprises an amino acid sequence selected from the group consisting of amino acid sequences SEQ ID NO. 6, 9, 11, 14, 17, 20, 22, 25, 29, 33, 35, and 46.

Current strategies that aim to exploit Vγ9Vδ2 T cells depend on their systemic activation (e.g. by aminobisphosphonates or synthetic phosphoantigens such as BrHPP) or on e.g. adoptive transfer of Vγ9Vδ2 T cells. These approaches have been shown to be well tolerated by patients and signs of antitumor activity have been documented. However, results are not consistent enough to allow widespread clinical application. Described strategies result in systemic activation of Vγ9Vδ2 T cells, but do not result in the specific recruitment of these cells to the tumour, where they are supposed to exert their antitumor effect. The said immunoglobulin molecule that activates human Vγ9Vδ2 T cells and that are preferably linked to an agent can be used to activate Vγ9Vδ2 T cells in a clinical setting.

Preferably, said immunoglobulin molecule that activates human Vγ9Vδ2 T cells are linked to an agent. Said agent is preferably an agent that can bind to a target, e.g. a cancer cell or an infected cell, e.g. infected with a virus, or a non-host cell, e.g. bacteria. Preferably said agent is an immunoglobulin molecule. More preferably, said immunoglobulin molecule is a single chain antibody or a single domain antibody. By linking to an agent, the agent can recruit and activate the human Vγ9Vδ2 T cells at the site where the action of the human Vγ9Vδ2 T cells is required, in contrast to systemic activation. For example, said immunoglobulin molecule that activates human Vγ9Vδ2 T cells can be linked to a tumour-specific antibody, an antiviral antibody, or an antibacterial antibody. Such a tumour specific antibody can be any antibody. Such an immunoglobulin molecule linked to another antibody can be referred to as a bispecific antibody. A bispecific antibody may also consist of a first immunoglobulin molecule comprising the CDR1, CDR2 and CDR3 regions according to the invention, which is a chain such as comprised in a single chain antibody, wherein the first immunoglobulin chain is paired with a second immunoglobulin molecule which is also a chain such as being comprised in a single chain antibody wherein the second immunoglobulin binds to the target. A bispecific antibody is thus formed that has two chains (similar to as depicted in FIG. 9B), each chain having a different single binding domain wherein one binding domain comprises CDR1, CDR2 and CDR3 in accordance with the invention and the other binding domain binds to the targets. Said immunoglobulin molecule that activates human Vγ9Vδ2 T cells and linked to an agent can also be a bispecific antibody that comprises two single domain antibodies, the first single domain antibody comprising the CDR1, CDR2 and CDR3 regions according to the invention, wherein the first single domain antibody is linked to a second single domain antibody wherein the second single domain antibody binds to the target.

Hence, in one embodiment, said immunoglobulin molecule that activates human Vγ9Vδ2 T cells, and which is preferably linked to an agent is for use in a medical treatment. Preferably the medical treatment is a treatment of cancer or of an infection.

In a further embodiment, the use is provided said immunoglobulin molecule that activates human Vγ9Vδ2 T cells for activating human Vγ9Vδ2 T cells. Such use is for instance useful in assays such as described in the examples.

In a further embodiment, said immunoglobulin molecule that activates human Vγ9Vδ2 T cells comprises a label. These immunoglobulin molecules are in particular useful for flow cytometry of cells expressing human Vγ9Vδ2 T cell receptor. The immunoglobulin molecule may comprise a tag, e.g. a myc tag as described in the examples or an his-tag or a fluorescent protein sequence, or it may be coupled to a suitable imaging dye. Furthermore, when coupled to e.g. magnetic beads, these immunoglobulin molecules can be used for the isolation and purification of these cells from cell suspensions including those from peripheral blood. As these immunoglobulins that activate human Vγ9Vδ2 T cells, these immunoglobulin molecules are in particular useful for selecting these cells while at the same time activating and expanding the cell population. Hence, the use is further provided of these immunoglobulin molecules for labelling and/or for selecting, and for activating human Vγ9Vδ2 T cells.

In a further aspect of the invention, an immunoglobulin molecule is provided wherein the immunoglobulin molecule is an immunoglobulin molecule that does not block activation of human Vγ9Vδ2 T cells; and does not activate human Vγ9Vδ2 T cells and wherein it is a human Vγ9Vδ2 T cell receptor binding immunoglobulin molecule, comprising a CDR1 region and a CDR2 region, wherein the CDR1 region comprises an amino acid sequence with at least 40% sequence identity with the amino acid sequence of SEQ ID NO. 31 GRTFSNYAMG; and wherein the CDR2 region comprises an amino acid sequence with at least 60% sequence identity with the amino acid sequence of SEQ ID NO. 32 AISWSGGSTYYADSVKG; and wherein preferably the immunoglobulin molecule is a single chain antibody. In one Jurkat cells after which unbound phages were incubated for 1 hour with Jurkat Vγ9Vδ2. Phages were eluted and infected to E. coli as described for first round selections. Bacteria were plated on LB/2% glucose/ampicillin plates to generate single bacterial colonies coding eluted VHH DNA.

Production and Purification of VHH

VHH DNA from individual clones were digested with Sfi1/BstEII and cloned into plasmid pMEK219, a derivative from pHen1 (Hoogenboom et al. Nucleic Acids Res 1991) with addition of a HC-V cassette to enable Sfi1/BstEII cloning, add a C-terminal myc- and 6× HIS-tag deletion of the genIII sequence. pMEK219-VHH was transformed to TG1 bacteria. An overnight culture was used to inoculate 2×TY medium plus 0.1% glucose and 100 ug/ml ampicillin. When $OD_{600}$ reached 0.5, IPTG was added to a final concentration of 1 mM. Protein production was allowed for 2-5 hours. Growth of all cultures was performed at 37° C. with shaking at 200-220 rpm. Protein production was stopped by spinning cultures for 15 minutes at 4° C. The bacterial pellet was suspended in PBS and frozen for at least 1 hour. Bacterial suspension was thawed, slightly shaken for 1 hour at 4° C. and spun at 4500 rpm for 30 minutes. Supernatant was incubated with washed Talon resin (Clontech, 1290 Terra Bella Ave. Mountain View, Calif., USA) for 1 hour at room temperature. Talon resin was washed 3× with PBS and 1× with 15 mM imidazole/PBS pH7 and eluted with 150 mM imidazole/PBS pH7. The eluted fraction was dialysed 2× against PBS. Purified VHH was checked by coomassie stained protein gel for purity.

Binding of VHH to Donor-Derived Vγ9Vδ2 T Cells or Jurkat Vγ9Vδ2 T Cells.

$5*10^4$ donor-derived Vγ9Vδ2 T cells were washed with FACS buffer. All incubations were performed in FACS buffer for 30 minutes at 4° C. Cells were incubated with 25 µl 500 nM VHH. After washing, cells were incubated with 10 µl 1:500 anti-myc tag antibody clone 4A6 (Merck Millipore, 290 Cocord Road Billerica, Mass., USA). After washing, cells were incubated with 10 µl 1:200 goat-anti-mouse F(ab)2 APC (Beckman Coulter, Fullerton, Calif., USA) for 30 minutes at 4° C. After a final washing step, VHH binding to cells was measured by flowcytometry (FACSCalibur, BD Biosciences).

Activation of Donor-Derived Vγ9Vδ2 T Cells by VHH

Flat bottom 96-well cell culture plates (Costar) were coated overnight with 50 µl 4 ug/ml mouse-anti-myc clone 9E10 (made in house) at 4° C. Wells were washed with PBS and blocked with 200 µl 4% BSA/PBS at room temperature for 30 minutes. Block was discarded and wells were incubated with 30 µl 500 nM VHH in PBS for 2 hours at room temperature. Wells were washed and $1\times10^4$ Vγ9Vδ2 T in 200 µl IMDM+(Schneiders F L, et al. Clin Immunol 2012; 142:194-200) were added per well and incubated overnight at 37° C. in a $CO_2$ incubator with humidified atmosphere in the presence of golgiplug (1:500) (BD Biosciences) for intracellular cytokine retention. Flowcytometry was then used to determine CD25, IFN-γ and Granzyme B expression (as described; Schneiders F L, et al. Clin Immunol 2012; 142:194-200 (CD25-PE (clone M-A251, #555432), IFN-γ APC (clone B27 #554702) both available from BD Pharmingen. Granzyme B PE (clone GB-12 #M2289) available from Sanquin, Amsterdam, The Netherlands).

Neutralization of Donor-Derived Vγ9Vδ2 T Cells by VHH

HeLa cells were incubated with indicated amounts of aminobisphosphonates (NBP; ABP Pamidronaat-DiNatrium, Pharmachemie, Haarlem, The Netherlands) for 2 hours at 37° C. in a $CO_2$ incubator with humidified atmosphere. Cells were then washed and seeded at $5*10^4$ in 100 µl IMDM+ per well in a flat bottom 96-well cell culture plate (Costar) and allowed to adhere for 2 hours at 37° C. in a $CO_2$ incubator with humidified atmosphere. Cells were washed with PBS and cultured in 100 µl IMDM+. Donor-derived Vγ9Vδ2 T cells were incubated with the indicated VHH concentration for 1 hour at 4° C. $75*10^3$ VHH-incubated Vγ9Vδ2 T cells were added to NBP-treated HeLa cell coated wells and incubated at 37° C. in a $CO_2$ incubator with humidified atmosphere. Cells were harvested with trypsin to a 96-wells round bottom plate, Golgiplug (1:500, BD Biosciences) was added for intracellular cytokine retention. Flowcytometry was used to determine CD25, IFN-γ and Granzyme B expression (as described; Schneiders F L, et al. Clin Immunol 2012; 142:194-200)

VHH Chain Specificity

A donor-derived Vγ9Vδ2 T cell line was stained with mouse-anti-human Vδ2-FITC and mouse-anti-human Vγ9-PE (both BD Biosciences) and sorted with FACS Aria (BD Biosciences) for the populations: single Vδ2 positive γє T-cells, single Vγ9 positive γє Tcells, Vγ9Vδ2 double positive γє T-cells and Vγ9Vδ2 double negative γє T-cells. Sorted cells were cultured in the same way as the donor-derived Vγ9Vδ2 T cell lines. For determining VHH specificity, $10^4$ cells of the resulting purified sorted cell lines were stained with VHH similar to the methodology as described for binding of VHH to donor-derived Vγ9Vδ2 T cells with the adjustment that 10 µl 1:80 goat-anti-mouse-F(ab)2 RPE (#R0480 from Dako, Glostrup, Denmark) was used for anti-myc antibody detection.

Results

The selected VHHs were tested for specificity as described above, and all 20 VHHs (see table 2) showed binding to Vγ9Vδ2 T cell receptor expressing Jurkat cells as well as primary Vγ9Vδ2 T cells, whereas they did not bind to Jurkat cells not expressing the Vγ9Vδ2 T cell receptor.

Immunoglobulin Molecules that Block Phosphoantigen Induced Activation

Clones 6F6 and 5E7 were characterized as nanobodies that block phosphoantigen-induced stimulation of Vγ9Vδ2 T cells. Both clones 6F6 and 5E7 are nanobodies that bind to the Vδ2 chain of the Vγ9Vδ2 T cell receptor. GrB, CD25 and IFN-gamma expression were similar to unstimulated controls, whereas the positive control showed relative high expression levels (see FIG. 2). In a dose response curve, upon exposure to phosphoantigen, dose dependent neutralization of phospoantigen induced Vγ9Vδ2 T cell activation was shown (see FIG. 3). It was further shown that the VHH 5E7 nanobody inhibits Vγ9Vδ2 T cell activation by aminobisphosphonates (ABP) in a dose dependent manner, i.e. a higher dose of 5E7 results in a relative stronger reduction of CD25 and CD107a expression, and a relative stronger reduction of interferon-γ and TNF-α production as well. The 5E7 nanobody was also shown to inhibit spontaneous lysis of Daudi cells by Vγ9Vδ2 T cells in a dose dependent manner, whereas a control nanobody did not show any significant effect. In the same assay, the nitrogen-containing bisphosphonate pamidronate was used to activate Vγ9Vδ2 T cells resulting in an enhanced lysis of Daudi cells. Again, the 5E7 nanobody reduced the lysis of the Daudi cells in a dose dependent manner. This indicates that any undesired activation of Vγ9Vδ2 T cells may be reduced by using a nanobody that blocks Vγ9Vδ2 T cell activation. Such a antibody that blocks Vγ9Vδ2 T cell activation may be an antibody that binds to the Vδ2 chain of the Vγ9Vδ2 T cell receptor.

Immunoglobulin Molecules that Induce Activation

Various VHHs were shown to activate Vγ9Vδ2 T cells as shown by an increase in CD25 expression and an increase in IFN-gamma expression (see FIG. 4). Furthermore, such VHHs showed a typical dose response as an increasing dose of VHHs resulted in an increasing CD25 expression as well (see FIG. 5, right panel). Such a VHH was also coupled to an immunoglobulin molecule and the effect on apoptosis of tumour cells studied (see FIG. 6). The bispecific VHH (anticancer cell binding and Vγ9Vδ2 T cell binding and activation) showed potent activity towards killing of tumour cells. A bispecific VHH was made by coupling of anti-Vγ9Vδ2 nanobody 6H4 to a nanobody against a tumor. As bispecific controls, an anti-Vγ9Vδ2 nanobody was coupled to a control nanobody, and an anti-tumor nanobody was coupled to a control nanobody. At the highest dose tested (10 nM), the controls only induced about 22% lysis of tumor cells. The bispecific VHH (or nanobody) binding both Vγ9Vδ2 T cells and tumor cells induced about 85% lysis of the tumor cells mediated by the Vγ9Vδ2 T cells. In a dose response curve, the percentage of lysis by the Vγ9Vδ2 T cells decreased with a lower dose (1 nM, about 80%, 100 pM about 78%, 10 pM about 50%, 1 pM about 23% and 0 about 24%). In a control experiment without (bispecific) nanobodies only using bisphosphonates, about 80% of tumor cell lysis was observed. These results show that tumor-specific lysis by Vγ9Vδ2 T cells can be enhanced by using bispecific VHHs (or nanobodies), wherein both the tumor and Vγ9Vδ2 T cells are targeted, and wherein the specific tumor targeting of Vγ9Vδ2 T cells induces activation of Vγ9Vδ2 T cells as well.

Immunoglobulin Molecules that do not Induce Activation and do not Block Phosphoantigen Activation Several VHHs (5D7, 5C7, 5B11 and 6C4) showed no activation of human Vγ9Vδ2 T cells, nor did it have an effect on blocking phosphoantigen human Vγ9Vδ2 T cell activation (FIG. 8 and FIG. 5, left panel). Such VHHs are useful for example in FACS sorting (see FIG. 7).

Magnetic Bead Separation

An anti-Vδ2 (e.g. 6H4) or Vγ9 nanobody (e.g. 6H1) was biotinylated and mixed with PBMCs. The cells were washed to remove unbound nanobody. Magnetic beads with streptavidin (such as available from Miltenyi Biotec) were added to the mixture and cells bound to the beads, via the biotinylated nanobody, separated from unbound cells using a magnetic separating column. PBMCs were FACS analysed with regard to Vγ9 and Vδ2 expression. Excellent purification was obtained with both anti-Vδ2 and Vγ9 nanobodies. For example, with nanobody 6H4 4.5% of the PBMCs expressed both chains, after magnetic bead separation, 97.4% of the cells were positive for both Vγ9 and Vδ2 chains. The fraction of cells that did not bind to the magnetic beads were negative for both Vγ9 and Vδ2 chains (0%).

TABLE 2

Binding of VHHs to γδ T-cells expressing Vγ9Vδ2 or not expressing Vγ9Vδ2 or expressing a single Vγ9 or Vδ2 chain.

| Nr | Ref | Vδ2 + | Vγ9+ | Vγ9Vδ2+ | Vγ9Vδ2− |
|---|---|---|---|---|---|
| 1 | 5C7 | +/− | − | +/− | − |
| 2 | 5E3 | − | ++ | ++ | − |
| 3 | 6H1 | − | ++ | ++ | − |
| 4 | 5G3 | − | ++ | ++ | − |
| 5 | 5C1 | +/− | ++ | ++ | − |
| 6 | 5D3 | ++ | − | ++ | − |
| 7 | 6E3 | ++ | − | ++ | − |
| 8 | 6H4 | ++ | − | ++ | − |
| 9 | 6C1 | ++ | − | ++ | − |
| 10 | 6H3 | ++ | +/− | ++ | − |
| 11 | 6G3 | ++ | − | ++ | − |
| 12 | 6F6 | ++ | − | ++ | − |
| 13 | 5C8 | ++ | − | ++ | − |
| 14 | 5E7 | ++ | − | ++ | − |
| 15 | 5F5 | ++ | − | ++ | − |
| 16 | 6A1 | ++ | − | ++ | − |
| 17 | 5D7 | ++ | − | ++ | − |
| 18 | 5B11 | − | − | + | − |
| 19 | 6C4 | +/− | ++ | ++ | − |
| 20 | 6E4 | ++ | − | ++ | − |

TABLE 3

Sequences.

| SEQ ID. | code | Description | | Sequence |
|---|---|---|---|---|
| 1 | 5C7 | CDR1 | B | GRTFSRYTMG |
| 2 | 5C7 | CDR2 | B | AISWSGGRTNFAGSVKG |
| 3 | 5C7 | CDR3 | B | DWLPVPGRESYDY |
| 4 | 5E3 | CDR1 | A | GRTFSSYAMG |
| 5 | 5E3 | CDR2 | A | AISWSGGTTYYADSVKG |
| 6 | 5E3 | CDR3 | A | SLDCSGPGCHTAEYDY |
| 7 | 6H1 | CDR1 | A | GRTFSEYAMG |
| 8 | 6H1 | CDR2 | A | AISWTGSKTYYADSVKG |
| 9 | 6H1 | CDR3 | A | SSDCSGPGCHTEEYDY |
| 4 | 5G3 | CDR1 | A | GRTFSSYAMG |
| 10 | 5G3 | CDR2 | A | AVSWSGGSTYYADSVKG |

TABLE 3-continued

Sequences.

| SEQ ID. | code | Description | Sequence | |
|---|---|---|---|---|
| 11 | 5G3 | CDR3 | A | SQDCSGPGCYTNEYDS |
| 12 | 5C1 | CDR1 | A | GSIFSNYAMA |
| 13 | 5C1 | CDR2 | A | AVSWSGGRTYYADSVKG |
| 14 | 5C1 | CDR3 | A | SLSCSGPGCSLEEYDY |
| 15 | 5D3 | CDR1 | A | GRPFSNYAMG |
| 16 | 5D3 | CDR2 | A | VISWSGGSTYYADSVKG |
| 17 | 5D3 | CDR3 | A | QFSGASTVVAGTALDYDY |
| 18 | 6E3 | CDR1 | A | GRPFSNYGMG |
| 19 | 6E3 | CDR2 | A | GISWSGGSTDYADSVKG |
| 20 | 6E3 | CDR3 | A | VFSGAETAYYPSDDYDY |
| 18 | 6H4 | CDR1 | A | GRPFSNYGMG |
| 19 | 6H4 | CDR2 | A | GISWSGGSTDYADSVKG |
| 20 | 6H4 | CDR3 | A | VFSGAETAYYPSDDYDY |
| 18 | 6C1 | CDR1 | A | GRPFSNYGMG |
| 19 | 6C1 | CDR2 | A | GISWSGGSTDYADSVKG |
| 20 | 6C1 | CDR3 | A | VFSGAETAYYPSDDYDY |
| 18 | 6H3 | CDR1 | A | GRPFSNYGMG |
| 21 | 6H3 | CDR2 | A | GITWSGGSTHYADLVKG |
| 22 | 6H3 | CDR3 | A | VFSGAETAYYPSTEYDY |
| 23 | 6G3 | CDR1 | A | GRPFNNYGMG |
| 24 | 6G3 | CDR2 | A | GISWSGGSTYYADSVKG |
| 25 | 6G3 | CDR3 | A | VFSGAETAQYPSYDYDY |
| 15 | 6F6 | CDR1 | PA | GRPFSNYAMG |
| 26 | 6F6 | CDR2 | PA | AVTWSGGSTYYADSVKG |
| 27 | 6F6 | CDR3 | PA | QFNGAENIVPATTTPTSYDY |
| 15 | 5C8 | CDR1 | A | GRPFSNYAMG |
| 28 | 5C8 | CDR2 | A | AISWSGGSTSYADSVKG |
| 29 | 5C8 | CDR3 | A | QFSGADYGFGRLGIRGYEYDY |
| 15 | 5E7 | CDR1 | PA | GRPFSNYAMG |
| 28 | 5E7 | CDR2 | PA | AISWSGGSTSYADSVKG |
| 30 | 5E7 | CDR3 | PA | QFSGADYGFGRLGIQGYEYDY |
| 31 | 5F5 | CDR1 | A | GRTFSNYAMG |
| 32 | 5F5 | CDR2 | A | AISWSGGSTYYADSVKG |
| 33 | 5F5 | CDR3 | A | MFSGSESQLVVVITNLYEYDY |
| 31 | 6A1 | CDR1 | A | GRTFSNYAMG |
| 34 | 6A1 | CDR2 | A | TISWSGGSTYYADSVKG |
| 35 | 6A1 | CDR3 | A | AFSGSDYANTKKEVEYDY |
| 31 | 5D7 | CDR1 | B | GRTFSNYAMG |

TABLE 3-continued

Sequences.

| SEQ ID. | code | Description | Sequence |
|---|---|---|---|
| 36 | 5D7 | CDR2 B | AISWSGGMTDHADSVKG |
| 37 | 5D7 | CDR3 B | AFAGDIPYGSSWYGDPTTYDY |
| 38 | 5B11 | CDR1 B | GRTSSTFSMA |
| 39 | 5B11 | CDR2 B | AINWSGGSTRYADSVSD |
| 40 | 5B11 | CDR3 B | RRGGIYYSTQNDYDY |
| 41 | 6C4 | CDR1 B | VRTFSDYRMG |
| 42 | 6C4 | CDR2 B | TISWSGGLTYYADSVKG |
| 43 | 6C4 | CDR3 B | GGGYAGGTYYHPEE |
| 44 | 6E4 | CDR1 A | GFTFDDYCIA |
| 45 | 6E4 | CDR2 A | CITTSDGSTYYADSVKG |
| 46 | 6E4 | CDR3 A | YFGYGCYGGAQDYRAMDY |
| 47 | 5C7 | VHH | EVQLVESGGGLVQAGDSLRLSCAASGRTFSRYTMGWFRQAPGKEREFVAAISWSGGRTNFAGSVKGRFTISRDNAKNTVYLQMNSLKPEDTAVYYCAADWLPVPGRESYDYWGQGTQVTVSS |
| 48 | 5E3 | VHH | EVQLVESGGGLVQAGGSLRLSCTASGRTFSSYAMGWFRQAPGKEREFVAAISWSGGTTYYADSVKGRFTISRDNAKNTVSLQMNSLKPEDTAVYFCAASLDCSGPGCHTAEYDYWGQGTQVTVSS |
| 49 | 6H1 | VHH | EVQLVESGGGLVQAGGSLRLSCAATGRTFSEYAMGWFRQAPGKEREFAAAISWIGSKTYYADSVKGRFTISRDNAKNTVYLQMNSLKPEDTAVYYCAASSDCSGPGCHTEEYDYWGQGTQVTVSS |
| 50 | 5G3 | VHH | EVQLVESGGGLVQAGGSLRLSCAASGRTFSSYAMGWFRQAPGKEREFVAAVSWSGGSTYYADSVKGRFTISRDNARNTVYLQMNSLNPEDTAVYYCAASQDCSGPGCYTNEYDSWGQGTQVTVSS |
| 51 | 5C1 | VHH | EVQLVESGGGLVQPGGSLRLSCAASGSIFSNYAMAWFRQAPEKERDFLAAVSWSGGRTYYADSVKGRFTISRDNAKNTVNLQMNSLKPEDTAVYYCAASLSCSGPGCSLEEYDYWGQGTQVTVSS |
| 52 | 5D3 | VHH | EVQLVESGGGLVQAGGSLRLSCAASGRPFSNYAMGWFRQAPGKEREFVTVISWSGGSTYYADSVKGRFTISRDNAKNTVYLQMNSLKPEDTAVYYCAAQFSGASTVVAGTALDYDYWGQGTRVTVSS |
| 53 | 6E3 | VHH | EVQLVESGGGLVQAGGSLRLSCAASGRPFSNYGMGWFRQAPGKKREFVAGISWSGGSTDYADSVKGRLTISRDNAKNTVYLQMNSLKPEDTAVYYCAAVFSGAETAYYPSDDYDYWGQGTQVTVSS |
| 54 | 6H4 | VHH | EVQLVESGGGLVQAGGSLRLSCAASGRPFSNYGMGWFRQAPGKKREFVAGISWSGGSTDYADSVKGRFTISRDNAKNTVYLQMNSLKPEDTAVYYCAAVFSGAETAYYPSDDYDYWGQGTQVTVSS |
| 55 | 6C1 | VHH | EVQLVESGGGLVQAGGSLRLSCAASGRPFSNYGMGWFRQAPGKKRESVAGISWSGGSTDYADSVKGRFTISRDNAKNTVYLQMNSLKPEDTAVYYCAAVFSGAETAYYPSDDYDYWGQGTQVTVSS |
| 56 | 6H3 | VHH | EVQLVESGGGLVQAGGSLRLSCAVSGRPFSNYGMGWFRQAPGKEREFVAGITWSGGSTHYADLVKGRFTISRDNAKNTVHLQMNSLKPEDTAVYYCAAVFSGAETAYYPSTEYDYWGQGTQVTVSS |

TABLE 3-continued

Sequences.

| SEQ ID. | code | Description | Sequence |
|---|---|---|---|
| 57 | 6G3 | VHH | EVQLVESGGGLVQAGGSLRLSCAASGRPFNNYGMGWFRQAPGKEREFVAGISWSGGSTYYADSVKGRFTISRDNAKNTVYLQMNSLKPEDTAVYYCAAVFSGAETAQYPSYDYDYWGQGTQVTVSS |
| 58 | 6F6 | VHH | EVQLVESGGGLVQAGGSLRLSCVASGRPFSNYAMGWFRQAPGKEREFVAVTWSGGSTYYADSVKGRFAISRDNAKNTVYLQMNSLKPEDTAVYYCAAQFNGAENIVPATTTPTSYDYWGQGTQVTVSS |
| 59 | 5C8 | VHH | EVQLVESGGGLVQAGGSLRLSCAASGRPFSNYAMGWFRQAPGKEREFVAAISWSGGSTSYADSVKGRFTISRDNAKNTVYLQMNSPKPEDTAIYYCAAQFSGADYGFGRLGIRGYEYDYWGQGTQVTVSS |
| 60 | 5E7 | VHH | EVQLVESGGGLVQAGGSLRLSCAASGRPFSNYAMGWFRQAPGKEREFVAAISWSGGSTSYADSVKGRFTISRDNAENTVYLQMNSPKPEDTAIYYCAAQFSGADYGFGRLGIQGYEYDYWGQGTQVTVSS |
| 61 | 5F5 | VHH | EVQLVESGGGLVQAGGSLRLSCAASGRTFSNYAMGWFRQAPGKEREFVAAISWSGGSTYYADSVKGRFTISRDNAKNTVYLQMNSLKPEDTAVYYCAAMFSGSESQLVVVITNLYEYDYWGQGTQVTVSS |
| 62 | 6A1 | VHH | EVQLVESGGGLVQAGGSLRLSCAASGRTFSNYAMGWFRQAPGKEREFVATISWSGGSTYYADSVKGRFTISRDNAKNTVYLQMNSLKPEDTAVYYCAAAFSGSDYANTKKEVEYDYWGQGTQVTVSS |
| 63 | 5D7 | VHH | 1EVQLVESGGGLVQAGGSLRLSCIASGRTFSNYAMGWFRQAPGKEREFVAAISWSGGMTDHADSVKGRFTISRDNAKNTVYLQMNSLKPEDTAVYYCAAAFAGDIPYGSSWYGDPTTYDYWGQGTQVTVSS |
| 64 | B11 | VHH | EVQLVESGGGLVQAGGSLRLSCAASGRTSSTFSMAWFRQAPRKEREFVAAINWSGGSTRYADSVSDRFAISRDNAKNTVYLQMNNLKPEDTAVYYCAARRGGIYYSTQNDYDYWGQGTQVTVSS |
| 65 | 6C4 | VHH | 3EVQLVESGGGLVQAGGSLRLSCAVSVRTFSDYRMGWFRQAPGKEREFVSTISWSGGLTYYADSVKGRFTISRDNSKNTLYLQMNSLKPEDTAVYYCAAGGGYAGGTYYHPEEWGQGTQVTVSS |
| 66 | 6E4 | VHH | EVQLVESGGGLVQAGGSLRLSCAASGFTFDDYCIAWFRQAPGKEREPVSCITTSDGSTYYADSVKGRFTISSDNAKNTVYLQMNRLKPEDTAVYYCAAYFGYGCYGGAQDYRAMDYWGKGTLVTVSS |
| 67 | 5C7 | FRW1 | EVQLVESGGGLVQAGDSLRLSCAAS |
| 68 | 5C7 | FRW2 | WFRQAPGKEREFVA |
| 69 | 5C7 | FRW3 | RFTISRDNAKNTVYLQMNSLKPEDTAVYYCAA |
| 70 | 5C7 | FRW4 | WGQGTQVTVSS |
| 71 | Human V gamma 9 chain | TCR | MLSLLHASTLAVLGALCVYGAGHLEQPQISSTKTLSKTARLECVVSGITISATSVYWYRERPGEVIQFLVSISYDGTVRKESGIPSGKFEVDRIPETSTSTLTIHNVEKQDIATYYCALWEAQQELGKKIKVFGPGTKLIITDKQLDADVSPKPTIFLPSIAETKLQKAGTYLCLLEKFFPDVIKIHWEEKKSNTILGSQEGNTMKTNDTYMKFSWLTVPEKSLDKEHRCIVRHENNKNGVDQEIIFPPIKTDVITMDPKDNCSKDANDTLLLQLTNTSAYYMYLLLLLKSVVYFAIITCCLLRRTAFCCNGEKS |

TABLE 3-continued

Sequences.

| SEQ ID. code | Description | Sequence |
|---|---|---|
| 72 | Human TCR V delta 2 chain | MQRISSLIHLSLFWAGVMSAIELVPEHQTVPVSIGVP ATLRCSMKGEAIGNYYINWYRKTQGNTMTFIYREKDI YGPGFKDNFQGDIDIAKNLAVLKILAPSERDEGSYYC ACDTLGMGGEYTDKLIFGKGTRVTVEPRSQPHTKPSV FVMKNGTNVACLVKEFYPKDIRINLVSSKKITEFDPA IVISPSGKYNAVKLGKYEDSNSVTCSVQHDNKTVHST DFEVKTDSTDHVKPKETENTKQPSKSCHKPKAIVHTE KVNMMSLTVLGLRMLFAKTVAVNFLLTAKLFFL |

(B = binding, not activating, not phosphoantigen activation (PA) blocking; A = activating; PA = blocks PA activation)

The invention claimed is:

1. A human Vγ9Vδ2 T cell receptor binding immunoglobulin molecule comprising a CDR1 region, a CDR2 region, and a CDR 3 region, wherein the CDR1 region comprises a 10-amino acid sequence with at least 80% sequence identity with the 10-amino acid sequence of SEQ ID NO. 31, the CDR2 region comprises a 17-amino acid sequence with at least 94% sequence identity with the 17-amino acid sequence of SEQ ID NO. 32 and the CDR3 region comprises the amino acid sequence set forth in SEQ ID NO. 29.

2. The immunoglobulin molecule according to claim 1, wherein the immunoglobulin molecule is a single chain antibody.

3. The immunoglobulin molecule according to claim 1, wherein the immunoglobulin molecule is a single domain antibody.

4. The immunoglobulin molecule according to claim 1, comprising one or more of the framework regions selected from the group of amino acid sequences of SEQ ID NOS. 67-70.

5. An immunoglobulin molecule according to claim 1, wherein the immunoglobulin molecule is an immunoglobulin molecule that activates human Vγ9Vδ2 T cells.

6. The immunoglobulin molecule according to claim 5, wherein the immunoglobulin molecule is linked to an agent.

7. The immunoglobulin molecule according to claim 1, which is a bispecific antibody comprising two single domain antibodies, the first single domain antibody comprising the CDR1, CDR2 and CDR3 regions as defined in claim 1, wherein the first single domain antibody is linked to a second single domain antibody, wherein the second single domain antibody binds to a target.

8. The immunoglobulin molecule according to claim 1, which is a bispecific antibody comprising two single domain antibodies, the first single domain antibody comprising the CDR1, CDR2 and CDR3 regions as defined in claim 1, wherein the first single domain antibody is linked to a second single domain antibody, wherein the second single domain antibody binds to a cancer cell.

9. The immunoglobulin molecule of claim 2, wherein the single chain antibody is a llama single chain antibody.

10. The immunoglobulin molecule of claim 2, wherein the single chain antibody is a human single chain antibody.

11. The immunoglobulin molecule of claim 3, wherein the single domain antibody is a llama single domain antibody.

12. The immunoglobulin molecule of claim 3, wherein the single domain antibody is a humanized single domain antibody.

13. A bispecific immunoglobulin molecule comprising a single domain antibody that activates human Vγ9Vδ2 T cells, where said single domain antibody comprising a CDR1 region, a CDR2 region, and a CDR 3 region, wherein the CDR1 region comprises a 10-amino acid sequence with at least 80% sequence identity with the 10-amino acid sequence of SEQ ID NO. 31, the CDR2 region comprises a 17-amino acid sequence with at least 94% sequence identity with the 17-amino acid sequence of SEQ ID NO. 32 and the CDR3 region comprises the amino acid sequence set forth in SEQ ID NO. 29, where said single domain antibody is linked to a target-specific antibody.

14. The bispecific immunoglobulin molecule according to claim 13, wherein the single domain antibody comprising one or more framework regions selected from the group of amino acid sequences of SEQ ID NO. 67-70.

15. The bispecific immunoglobulin molecule according to claim 13, wherein said target-specific antibody is a tumor-antigen-specific antibody.

16. The bispecific immunoglobulin molecule according to claim 13, wherein the single domain antibody is a llama single domain antibody.

17. A bispecific immunoglobulin molecule comprising a VHH that activates human Vγ9Vδ2 T cells, where said VHH comprises a CDR1 region, a CDR2 region, and a CDR 3 region, wherein the CDR1 region comprises a 10-amino acid sequence with at least 80% sequence identity with the 10-amino acid sequence of SEQ ID NO. 31, the CDR2 region comprises a 17-amino acid sequence with at least 94% sequence identity with the 17-amino acid sequence of SEQ ID NO. 32 and the CDR3 region comprises the amino acid sequence set forth in SEQ ID NO. 29, where said VHH is linked to a target-specific antibody and binds the Vδ2 chain of a Vγ9Vδ2 T cell receptor.

18. The bispecific immunoglobulin molecule according to claim 17, wherein the VHH comprising one or more framework regions selected from the group of amino acid sequences of SEQ ID NO. 67-70.

19. The bispecific immunoglobulin molecule according to claim 17, wherein said target-specific antibody is a tumor-antigen-specific antibody.

20. The bispecific immunoglobulin molecule according to claim 17, wherein the single domain antibody is a llama single domain antibody.

21. A method for the treatment of cancer comprising administering to a subject in need thereof a bispecific immunoglobulin molecule comprising a single domain antibody that activates human Vγ9Vδ2 T cells, where said antibody comprises a CDR1 region, a CDR2 region, and a CDR 3 region, wherein the CDR1 region comprises a 10-amino acid sequence with at least 80% sequence identity with the 10-amino acid sequence of SEQ ID NO. 31, the CDR2 region comprises a 17-amino acid sequence with at least 94% sequence identity with the 17-amino acid sequence of SEQ ID NO. 32 and the CDR3 region comprises the amino acid sequence set forth in SEQ ID NO. 29, linked to a tumor-antigen specific antibody, wherein said antibody that activates human Vγ9Vδ2 T cells binds the Vδ2 chain of a Vγ9Vδ2 T cell receptor.

\* \* \* \* \*

UNITED STATES PATENT AND TRADEMARK OFFICE
CERTIFICATE OF CORRECTION

PATENT NO. : 11,384,145 B2
APPLICATION NO. : 17/513621
DATED : July 12, 2022
INVENTOR(S) : Johannes Jelle Van Der Vliet et al.

It is certified that error appears in the above-identified patent and that said Letters Patent is hereby corrected as shown below:

In the Claims

Claim 10, Column 65, Line 55: "human" should read as "humanized".

Signed and Sealed this
Eleventh Day of October, 2022

*Katherine Kelly Vidal*

Katherine Kelly Vidal
*Director of the United States Patent and Trademark Office*

SEQUENCE LISTING

<160> NUMBER OF SEQ ID NOS: 72

<210> SEQ ID NO 1
<211> LENGTH: 10
<212> TYPE: PRT
<213> ORGANISM: Llama glama

<400> SEQUENCE: 1

Gly Arg Thr Phe Ser Arg Tyr Thr Met Gly
1               5                   10

<210> SEQ ID NO 2
<211> LENGTH: 17
<212> TYPE: PRT
<213> ORGANISM: Llama glama

<400> SEQUENCE: 2

Ala Ile Ser Trp Ser Gly Gly Arg Thr Asn Phe Ala Gly Ser Val Lys
1               5                   10                  15
Gly

<210> SEQ ID NO 3
<211> LENGTH: 13
<212> TYPE: PRT
<213> ORGANISM: Llama glama

<400> SEQUENCE: 3

Asp Trp Leu Pro Val Pro Gly Arg Glu Ser Tyr Asp Tyr
1               5                   10

<210> SEQ ID NO 4
<211> LENGTH: 10
<212> TYPE: PRT
<213> ORGANISM: Llama glama

<400> SEQUENCE: 4

Gly Arg Thr Phe Ser Ser Tyr Ala Met Gly
1               5                   10

<210> SEQ ID NO 5
<211> LENGTH: 17
<212> TYPE: PRT
<213> ORGANISM: Llama glama

<400> SEQUENCE: 5

Ala Ile Ser Trp Ser Gly Gly Thr Thr Tyr Tyr Ala Asp Ser Val Lys
1               5                   10                  15

Gly

<210> SEQ ID NO 6
<211> LENGTH: 16
<212> TYPE: PRT
<213> ORGANISM: Llama glama

<400> SEQUENCE: 6

Ser Leu Asp Cys Ser Gly Pro Gly Cys His Thr Ala Glu Tyr Asp Tyr
1               5                   10                  15

<210> SEQ ID NO 7
<211> LENGTH: 10
<212> TYPE: PRT
<213> ORGANISM: Llama glama

<400> SEQUENCE: 7

Gly Arg Thr Phe Ser Glu Tyr Ala Met Gly
1               5                   10

<210> SEQ ID NO 8
<211> LENGTH: 17
<212> TYPE: PRT
<213> ORGANISM: Llama glama

<400> SEQUENCE: 8

Ala Ile Ser Trp Thr Gly Ser Lys Thr Tyr Tyr Ala Asp Ser Val Lys
1               5                   10                  15
Gly

<210> SEQ ID NO 9
<211> LENGTH: 16
<212> TYPE: PRT
<213> ORGANISM: Llama glama

<400> SEQUENCE: 9

Ser Ser Asp Cys Ser Gly Pro Gly Cys His Thr Glu Glu Tyr Asp Tyr
1               5                   10                  15

<210> SEQ ID NO 10
<211> LENGTH: 17
<212> TYPE: PRT
<213> ORGANISM: Llama glama

<400> SEQUENCE: 10

Ala Val Ser Trp Ser Gly Gly Ser Thr Tyr Tyr Ala Asp Ser Val Lys
1               5                   10                  15
Gly

<210> SEQ ID NO 11
<211> LENGTH: 16
<212> TYPE: PRT
<213> ORGANISM: Llama glama

<400> SEQUENCE: 11

Ser Gln Asp Cys Ser Gly Pro Gly Cys Tyr Thr Asn Glu Tyr Asp Ser
1               5                   10                  15

<210> SEQ ID NO 12
<211> LENGTH: 10
<212> TYPE: PRT
<213> ORGANISM: Llama glama

<400> SEQUENCE: 12

Gly Ser Ile Phe Ser Asn Tyr Ala Met Ala
1               5                   10

<210> SEQ ID NO 13
<211> LENGTH: 17
<212> TYPE: PRT
<213> ORGANISM: Llama glama

<400> SEQUENCE: 13

Ala Val Ser Trp Ser Gly Gly Arg Thr Tyr Tyr Ala Asp Ser Val Lys
1               5                   10                  15

Gly

<210> SEQ ID NO 14
<211> LENGTH: 16
<212> TYPE: PRT
<213> ORGANISM: Llama glama

<400> SEQUENCE: 14

Ser Leu Ser Cys Ser Gly Pro Gly Cys Ser Leu Glu Glu Tyr Asp Tyr
1               5                   10                  15

<210> SEQ ID NO 15
<211> LENGTH: 10
<212> TYPE: PRT
<213> ORGANISM: Llama glama

<400> SEQUENCE: 15

Gly Arg Pro Phe Ser Asn Tyr Ala Met Gly
1               5                   10

<210> SEQ ID NO 16
<211> LENGTH: 17
<212> TYPE: PRT
<213> ORGANISM: Llama glama

<400> SEQUENCE: 16

Val Ile Ser Trp Ser Gly Gly Ser Thr Tyr Tyr Ala Asp Ser Val Lys
1               5                   10                  15

Gly

<210> SEQ ID NO 17
<211> LENGTH: 18
<212> TYPE: PRT
<213> ORGANISM: Llama glama

<400> SEQUENCE: 17

Gln Phe Ser Gly Ala Ser Thr Val Val Ala Gly Thr Ala Leu Asp Tyr
1               5                   10                  15

Asp Tyr

<210> SEQ ID NO 18
<211> LENGTH: 10
<212> TYPE: PRT
<213> ORGANISM: Llama glama

<400> SEQUENCE: 18

Gly Arg Pro Phe Ser Asn Tyr Gly Met Gly
1               5                   10

<210> SEQ ID NO 19

-continued

```
<211> LENGTH: 17
<212> TYPE: PRT
<213> ORGANISM: Llama glama

<400> SEQUENCE: 19

Gly Ile Ser Trp Ser Gly Gly Ser Thr Asp Tyr Ala Asp Ser Val Lys
1               5                   10                  15

Gly

<210> SEQ ID NO 20
<211> LENGTH: 17
<212> TYPE: PRT
<213> ORGANISM: Llama glama

<400> SEQUENCE: 20

Val Phe Ser Gly Ala Glu Thr Ala Tyr Tyr Pro Ser Asp Asp Tyr Asp
1               5                   10                  15

Tyr

<210> SEQ ID NO 21
<211> LENGTH: 17
<212> TYPE: PRT
<213> ORGANISM: Llama glama

<400> SEQUENCE: 21

Gly Ile Thr Trp Ser Gly Gly Ser Thr His Tyr Ala Asp Leu Val Lys
1               5                   10                  15

Gly

<210> SEQ ID NO 22
<211> LENGTH: 17
<212> TYPE: PRT
<213> ORGANISM: Llama glama

<400> SEQUENCE: 22

Val Phe Ser Gly Ala Glu Thr Ala Tyr Tyr Pro Ser Thr Glu Tyr Asp
1               5                   10                  15

Tyr

<210> SEQ ID NO 23
<211> LENGTH: 10
<212> TYPE: PRT
<213> ORGANISM: Llama glama

<400> SEQUENCE: 23

Gly Arg Pro Phe Asn Asn Tyr Gly Met Gly
1               5                   10

<210> SEQ ID NO 24
<211> LENGTH: 17
<212> TYPE: PRT
<213> ORGANISM: Llama glama

<400> SEQUENCE: 24

Gly Ile Ser Trp Ser Gly Gly Ser Thr Tyr Tyr Ala Asp Ser Val Lys
1               5                   10                  15

Gly

<210> SEQ ID NO 25
<211> LENGTH: 17
<212> TYPE: PRT
<213> ORGANISM: Llama glama
```

```
<400> SEQUENCE: 25

Val Phe Ser Gly Ala Glu Thr Ala Gln Tyr Pro Ser Tyr Asp Tyr Asp
1               5                   10                  15

Tyr

<210> SEQ ID NO 26
<211> LENGTH: 17
<212> TYPE: PRT
<213> ORGANISM: Llama glama

<400> SEQUENCE: 26

Ala Val Thr Trp Ser Gly Gly Ser Thr Tyr Tyr Ala Asp Ser Val Lys
1               5                   10                  15

Gly

<210> SEQ ID NO 27
<211> LENGTH: 20
<212> TYPE: PRT
<213> ORGANISM: Llama glama

<400> SEQUENCE: 27

Gln Phe Asn Gly Ala Glu Asn Ile Val Pro Ala Thr Thr Thr Pro Thr
1               5                   10                  15

Ser Tyr Asp Tyr
            20

<210> SEQ ID NO 28
<211> LENGTH: 17
<212> TYPE: PRT
<213> ORGANISM: Llama glama

<400> SEQUENCE: 28

Ala Ile Ser Trp Ser Gly Gly Ser Thr Ser Tyr Ala Asp Ser Val Lys
1               5                   10                  15

Gly

<210> SEQ ID NO 29
<211> LENGTH: 21
<212> TYPE: PRT
<213> ORGANISM: Llama glama

<400> SEQUENCE: 29

Gln Phe Ser Gly Ala Asp Tyr Gly Phe Gly Arg Leu Gly Ile Arg Gly
1               5                   10                  15

Tyr Glu Tyr Asp Tyr
            20

<210> SEQ ID NO 30
<211> LENGTH: 21
<212> TYPE: PRT
<213> ORGANISM: Llama glama

<400> SEQUENCE: 30

Gln Phe Ser Gly Ala Asp Tyr Gly Phe Gly Arg Leu Gly Ile Gln Gly
1               5                   10                  15

Tyr Glu Tyr Asp Tyr
            20

<210> SEQ ID NO 31
<211> LENGTH: 10
```

```
<212> TYPE: PRT
<213> ORGANISM: Llama glama

<400> SEQUENCE: 31

Gly Arg Thr Phe Ser Asn Tyr Ala Met Gly
1               5                   10

<210> SEQ ID NO 32
<211> LENGTH: 17
<212> TYPE: PRT
<213> ORGANISM: Llama glama

<400> SEQUENCE: 32

Ala Ile Ser Trp Ser Gly Gly Ser Thr Tyr Tyr Ala Asp Ser Val Lys
1               5                   10                  15

Gly

<210> SEQ ID NO 33
<211> LENGTH: 21
<212> TYPE: PRT
<213> ORGANISM: Llama glama

<400> SEQUENCE: 33

Met Phe Ser Gly Ser Glu Ser Gln Leu Val Val Val Ile Thr Asn Leu
1               5                   10                  15

Tyr Glu Tyr Asp Tyr
            20

<210> SEQ ID NO 34
<211> LENGTH: 17
<212> TYPE: PRT
<213> ORGANISM: Llama glama

<400> SEQUENCE: 34

Thr Ile Ser Trp Ser Gly Gly Ser Thr Tyr Tyr Ala Asp Ser Val Lys
1               5                   10                  15

Gly

<210> SEQ ID NO 35
<211> LENGTH: 18
<212> TYPE: PRT
<213> ORGANISM: Llama glama

<400> SEQUENCE: 35

Ala Phe Ser Gly Ser Asp Tyr Ala Asn Thr Lys Lys Glu Val Glu Tyr
1               5                   10                  15

Asp Tyr

<210> SEQ ID NO 36
<211> LENGTH: 17
<212> TYPE: PRT
<213> ORGANISM: Llama glama

<400> SEQUENCE: 36

Ala Ile Ser Trp Ser Gly Gly Met Thr Asp His Ala Asp Ser Val Lys
1               5                   10                  15

Gly

<210> SEQ ID NO 37
<211> LENGTH: 21
<212> TYPE: PRT
<213> ORGANISM: Llama glama
```

```
<400> SEQUENCE: 37

Ala Phe Ala Gly Asp Ile Pro Tyr Gly Ser Ser Trp Tyr Gly Asp Pro
1               5                   10                  15

Thr Thr Tyr Asp Tyr
            20

<210> SEQ ID NO 38
<211> LENGTH: 10
<212> TYPE: PRT
<213> ORGANISM: Llama glama

<400> SEQUENCE: 38

Gly Arg Thr Ser Ser Thr Phe Ser Met Ala
1               5                   10

<210> SEQ ID NO 39
<211> LENGTH: 17
<212> TYPE: PRT
<213> ORGANISM: Llama glama

<400> SEQUENCE: 39

Ala Ile Asn Trp Ser Gly Gly Ser Thr Arg Tyr Ala Asp Ser Val Ser
1               5                   10                  15

Asp

<210> SEQ ID NO 40
<211> LENGTH: 15
<212> TYPE: PRT
<213> ORGANISM: Llama glama

<400> SEQUENCE: 40

Arg Arg Gly Gly Ile Tyr Tyr Ser Thr Gln Asn Asp Tyr Asp Tyr
1               5                   10                  15

<210> SEQ ID NO 41
<211> LENGTH: 10
<212> TYPE: PRT
<213> ORGANISM: Llama glama

<400> SEQUENCE: 41

Val Arg Thr Phe Ser Asp Tyr Arg Met Gly
1               5                   10

<210> SEQ ID NO 42
<211> LENGTH: 17
<212> TYPE: PRT
<213> ORGANISM: Llama glama

<400> SEQUENCE: 42

Thr Ile Ser Trp Ser Gly Gly Leu Thr Tyr Tyr Ala Asp Ser Val Lys
1               5                   10                  15

Gly

<210> SEQ ID NO 43
<211> LENGTH: 14
<212> TYPE: PRT
<213> ORGANISM: Llama glama

<400> SEQUENCE: 43

Gly Gly Gly Tyr Ala Gly Gly Thr Tyr Tyr His Pro Glu Glu
1               5                   10
```

```
<210> SEQ ID NO 44
<211> LENGTH: 10
<212> TYPE: PRT
<213> ORGANISM: Llama glama

<400> SEQUENCE: 44

Gly Phe Thr Phe Asp Asp Tyr Cys Ile Ala
1               5                   10

<210> SEQ ID NO 45
<211> LENGTH: 17
<212> TYPE: PRT
<213> ORGANISM: Llama glama

<400> SEQUENCE: 45

Cys Ile Thr Thr Ser Asp Gly Ser Thr Tyr Tyr Ala Asp Ser Val Lys
1               5                   10                  15

Gly

<210> SEQ ID NO 46
<211> LENGTH: 18
<212> TYPE: PRT
<213> ORGANISM: Llama glama

<400> SEQUENCE: 46

Tyr Phe Gly Tyr Gly Cys Tyr Gly Gly Ala Gln Asp Tyr Arg Ala Met
1               5                   10                  15

Asp Tyr

<210> SEQ ID NO 47
<211> LENGTH: 122
<212> TYPE: PRT
<213> ORGANISM: Llama glama

<400> SEQUENCE: 47

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Arg Tyr
            20                  25                  30

Thr Met Gly Trp Phe Arg Gln Ala Pro Gly Lys Glu Arg Glu Phe Val
        35                  40                  45

Ala Ala Ile Ser Trp Ser Gly Arg Thr Asn Phe Ala Gly Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Trp Leu Pro Val Pro Gly Arg Glu Ser Tyr Asp Tyr Trp
            100                 105                 110

Gly Gln Gly Thr Gln Val Thr Val Ser Ser
        115                 120

<210> SEQ ID NO 48
<211> LENGTH: 125
<212> TYPE: PRT
<213> ORGANISM: Llama glama

<400> SEQUENCE: 48

Glu Val Gln Leu Val Glu Ser Gly Gly Gly Leu Val Gln Ala Gly Gly
1               5                   10                  15
```

Ser Leu Arg Leu Ser Cys Thr Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Thr Thr Tyr Ala Asp Ser Val
    50                  55                  60

Lys Gly Arg Phe Thr Ile Ser Arg Asp Asn Ala Lys Asn Thr Val Ser
65                  70                  75                  80

Leu Gln Met Asn Ser Leu Lys Pro Glu Asp Thr Ala Val Tyr Phe Cys
                85                  90                  95

Ala Ala Ser Leu Asp Cys Ser Gly Pro Gly Cys His Thr Ala Glu Tyr
            100                 105                 110

Asp Tyr Trp Gly Gln Gly Thr Gln Val Thr Val Ser Ser
        115                 120                 125

<210> SEQ ID NO 49
<211> LENGTH: 125
<212> TYPE: PRT
<213> ORGANISM: Llama glama

<400> SEQUENCE: 49

Glu Val Gln Leu Val Glu Ser Gly Gly Gly Leu Val Gln Ala Gly Gly
1               5                   10                  15

Ser Leu Arg Leu Ser Cys Ala Ala Thr Gly Arg Thr Phe Ser Glu Tyr
            20                  25                  30

Ala Met Gly Trp Phe Arg Gln Ala Pro Gly Lys Glu Arg Glu Phe Ala
        35                  40                  45

Ala Ala Ile Ser Trp Thr Gly Ser Lys Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Ser Asp Cys Ser Gly Pro Gly Cys His Thr Glu Glu Tyr
            100                 105                 110

Asp Tyr Trp Gly Gln Gly Thr Gln Val Thr Val Ser Ser
        115                 120                 125

<210> SEQ ID NO 50
<211> LENGTH: 125
<212> TYPE: PRT
<213> ORGANISM: Llama glama

<400> SEQUENCE: 50

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Val Ser Trp Ser Gly Ser Thr Tyr Tyr Ala Asp Ser Val
    50                  55                  60

Lys Gly Arg Phe Thr Ile Ser Arg Asp Asn Ala Arg Asn Thr Val Tyr
65                  70                  75                  80

Leu Gln Met Asn Ser Leu Asn Pro Glu Asp Thr Ala Val Tyr Tyr Cys
                85                  90                  95

```
Ala Ala Ser Gln Asp Cys Ser Gly Pro Gly Cys Tyr Thr Asn Glu Tyr
            100                 105                 110

Asp Ser Trp Gly Gln Gly Thr Gln Val Thr Val Ser Ser
        115                 120                 125

<210> SEQ ID NO 51
<211> LENGTH: 125
<212> TYPE: PRT
<213> ORGANISM: Llama glama

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Asn Tyr
            20                  25                  30

Ala Met Ala Trp Phe Arg Gln Ala Pro Glu Lys Glu Arg Asp Phe Leu
        35                  40                  45

Ala Ala Val Ser Trp Ser Gly Arg Thr Tyr Tyr Ala Asp Ser Val
    50                  55                  60

Lys Gly Arg Phe Thr Ile Ser Arg Asp Asn Ala Lys Asn Thr Val Asn
65                  70                  75                  80

Leu Gln Met Asn Ser Leu Lys Pro Glu Asp Thr Ala Val Tyr Tyr Cys
                85                  90                  95

Ala Ala Ser Leu Ser Cys Ser Gly Pro Gly Cys Ser Leu Glu Glu Tyr
            100                 105                 110

Asp Tyr Trp Gly Gln Gly Thr Gln Val Thr Val Ser Ser
        115                 120                 125

<210> SEQ ID NO 52
<211> LENGTH: 127
<212> TYPE: PRT
<213> ORGANISM: Llama glama

<400> SEQUENCE: 52

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser Asn Tyr
            20                  25                  30

Ala Met Gly Trp Phe Arg Gln Ala Pro Gly Lys Glu Arg Glu Phe Val
        35                  40                  45

Thr Val Ile Ser Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gln Phe Ser Gly Ala Ser Thr Val Val Ala Gly Thr Ala Leu
            100                 105                 110

Asp Tyr Asp Tyr Trp Gly Gln Gly Thr Arg Val Thr Val Ser Ser
        115                 120                 125

<210> SEQ ID NO 53
<211> LENGTH: 126
<212> TYPE: PRT
<213> ORGANISM: Llama glama

<400> SEQUENCE: 53
```

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser Asn Tyr
            20                  25                  30

Gly Met Gly Trp Phe Arg Gln Ala Pro Gly Lys Lys Arg Glu Phe Val
        35                  40                  45

Ala Gly Ile Ser Trp Ser Gly Ser Thr Asp Tyr Ala Asp Ser Val
    50                  55                  60

Lys Gly Arg Leu Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Phe Ser Gly Ala Glu Thr Ala Tyr Tyr Pro Ser Asp Asp
            100                 105                 110

Tyr Asp Tyr Trp Gly Gln Gly Thr Gln Val Thr Val Ser Ser
            115                 120                 125
```

<210> SEQ ID NO 54
<211> LENGTH: 126
<212> TYPE: PRT
<213> ORGANISM: Llama glama

<400> SEQUENCE: 54

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser Asn Tyr
            20                  25                  30

Gly Met Gly Trp Phe Arg Gln Ala Pro Gly Lys Lys Arg Glu Phe Val
        35                  40                  45

Ala Gly Ile Ser Trp Ser Gly Ser Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Phe Ser Gly Ala Glu Thr Ala Tyr Tyr Pro Ser Asp Asp
            100                 105                 110

Tyr Asp Tyr Trp Gly Gln Gly Thr Gln Val Thr Val Ser Ser
            115                 120                 125
```

<210> SEQ ID NO 55
<211> LENGTH: 126
<212> TYPE: PRT
<213> ORGANISM: Llama glama

<400> SEQUENCE: 55

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser Asn Tyr
            20                  25                  30

Gly Met Gly Trp Phe Arg Gln Ala Pro Gly Lys Lys Arg Glu Ser Val
        35                  40                  45

Ala Gly Ile Ser Trp Ser Gly Ser Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Lys Pro Glu Asp Thr Ala Val Tyr Tyr Cys
                85                  90                  95

Ala Ala Val Phe Ser Gly Ala Glu Thr Ala Tyr Tyr Pro Ser Asp Asp
            100                 105                 110

Tyr Asp Tyr Trp Gly Gln Gly Thr Gln Val Thr Val Ser Ser
        115                 120                 125
```

<210> SEQ ID NO 56
<211> LENGTH: 126
<212> TYPE: PRT
<213> ORGANISM: Llama glama

<400> SEQUENCE: 56

```
Glu Val Gln Leu Val Glu Ser Gly Gly Gly Leu Val Gln Ala Gly Gly
1               5                   10                  15

Ser Leu Arg Leu Ser Cys Ala Val Ser Gly Arg Pro Phe Ser Asn Tyr
            20                  25                  30

Gly Met Gly Trp Phe Arg Gln Ala Pro Gly Lys Glu Arg Glu Phe Val
        35                  40                  45

Ala Gly Ile Thr Trp Ser Gly Ser Thr His Tyr Ala Asp Leu Val
    50                  55                  60

Lys Gly Arg Phe Thr Ile Ser Arg Asp Asn Ala Lys Asn Thr Val His
65                  70                  75                  80

Leu Gln Met Asn Ser Leu Lys Pro Glu Asp Thr Ala Val Tyr Tyr Cys
                85                  90                  95

Ala Ala Val Phe Ser Gly Ala Glu Thr Ala Tyr Tyr Pro Ser Thr Glu
            100                 105                 110

Tyr Asp Tyr Trp Gly Gln Gly Thr Gln Val Thr Val Ser Ser
        115                 120                 125
```

<210> SEQ ID NO 57
<211> LENGTH: 126
<212> TYPE: PRT
<213> ORGANISM: Llama glama

<400> SEQUENCE: 57

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Asn Asn Tyr
            20                  25                  30

Gly Met Gly Trp Phe Arg Gln Ala Pro Gly Lys Glu Arg Glu Phe Val
        35                  40                  45

Ala Gly Ile Ser Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Val Phe Ser Gly Ala Glu Thr Ala Gln Tyr Pro Ser Tyr Asp
            100                 105                 110

Tyr Asp Tyr Trp Gly Gln Gly Thr Gln Val Thr Val Ser Ser
        115                 120                 125
```

<210> SEQ ID NO 58
<211> LENGTH: 129
<212> TYPE: PRT
<213> ORGANISM: Llama glama

<400> SEQUENCE: 58

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Pro Phe Ser Asn Tyr
            20                  25                  30

Ala Met Gly Trp Phe Arg Gln Ala Pro Gly Lys Glu Arg Glu Phe Val
        35                  40                  45

Ala Ala Val Thr Trp Ser Gly Ser Thr Tyr Tyr Ala Asp Ser Val
    50                  55                  60

Lys Gly Arg Phe Ala Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gln Phe Asn Gly Ala Glu Asn Ile Val Pro Ala Thr Thr Thr
            100                 105                 110

Pro Thr Ser Tyr Asp Tyr Trp Gly Gln Gly Thr Gln Val Thr Val Ser
        115                 120                 125

Ser

<210> SEQ ID NO 59
<211> LENGTH: 130
<212> TYPE: PRT
<213> ORGANISM: Llama glama

<400> SEQUENCE: 59

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ser Thr Ser Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Pro Lys Pro Glu Asp Thr Ala Ile Tyr Tyr Cys
                85                  90                  95

Ala Ala Gln Phe Ser Gly Ala Asp Tyr Gly Phe Gly Arg Leu Gly Ile
            100                 105                 110

Arg Gly Tyr Glu Tyr Asp Tyr Trp Gly Gln Gly Thr Gln Val Thr Val
        115                 120                 125

Ser Ser
    130

<210> SEQ ID NO 60
<211> LENGTH: 130
<212> TYPE: PRT
<213> ORGANISM: Llama glama

<400> SEQUENCE: 60

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Pro Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Ser Tyr Ala Asp Ser Val
            50                  55                  60

Lys Gly Arg Phe Thr Ile Ser Arg Asp Asn Ala Glu Asn Thr Val Tyr
 65                  70                  75                  80

Leu Gln Met Asn Ser Pro Lys Pro Glu Asp Thr Ala Ile Tyr Tyr Cys
                85                  90                  95

Ala Ala Gln Phe Ser Gly Ala Asp Tyr Gly Phe Gly Arg Leu Gly Ile
            100                 105                 110

Gln Gly Tyr Glu Tyr Asp Tyr Trp Gly Gln Gly Thr Gln Val Thr Val
            115                 120                 125

Ser Ser
    130

<210> SEQ ID NO 61
<211> LENGTH: 130
<212> TYPE: PRT
<213> ORGANISM: Llama glama

<400> SEQUENCE: 61

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
            35                  40                  45

Ala Ala Ile Ser Trp Ser Gly Gly Ser Thr Tyr Tyr Ala Asp Ser Val
            50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Ala Met Phe Ser Gly Ser Glu Ser Gln Leu Val Val Val Ile Thr
            100                 105                 110

Asn Leu Tyr Glu Tyr Asp Tyr Trp Gly Gln Gly Thr Gln Val Thr Val
            115                 120                 125

Ser Ser
    130

<210> SEQ ID NO 62
<211> LENGTH: 127
<212> TYPE: PRT
<213> ORGANISM: Llama glama

<400> SEQUENCE: 62

Glu Val Gln Leu Val Glu Ser Gly Gly Gly Leu Val Gln Ala Gly Gly
 1               5                  10                  15

Ser Leu Arg Leu Ser Cys Ala Ser Gly Arg Thr Phe Ser Asn Tyr
            20                  25                  30

Ala Met Gly Trp Phe Arg Gln Ala Pro Gly Lys Glu Arg Glu Phe Val
            35                  40                  45

Ala Thr Ile Ser Trp Ser Gly Ser Thr Tyr Tyr Ala Asp Ser Val
            50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

```
Ala Ala Ala Phe Ser Gly Ser Asp Tyr Ala Asn Thr Lys Lys Glu Val
            100                 105                 110

Glu Tyr Asp Tyr Trp Gly Gln Gly Thr Gln Val Thr Val Ser Ser
        115                 120                 125
```

<210> SEQ ID NO 63
<211> LENGTH: 130
<212> TYPE: PRT
<213> ORGANISM: Llama glama

<400> SEQUENCE: 63

```
Glu Val Gln Leu Val Glu Ser Gly Gly Gly Leu Val Gln Ala Gly Gly
1               5                   10                  15

Ser Leu Arg Leu Ser Cys Ile Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Met Thr Asp His Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Phe Ala Gly Asp Ile Pro Tyr Gly Ser Ser Trp Tyr Gly
            100                 105                 110

Asp Pro Thr Thr Tyr Asp Tyr Trp Gly Gln Gly Thr Gln Val Thr Val
        115                 120                 125

Ser Ser
    130
```

<210> SEQ ID NO 64
<211> LENGTH: 124
<212> TYPE: PRT
<213> ORGANISM: Llama glama

<400> SEQUENCE: 64

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Thr Phe
            20                  25                  30

Ser Met Ala Trp Phe Arg Gln Ala Pro Arg Lys Glu Arg Glu Phe Val
        35                  40                  45

Ala Ala Ile Asn Trp Ser Gly Ser Thr Arg Tyr Ala Asp Ser Val
    50                  55                  60

Ser Asp Arg Phe Ala Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Ala Arg Arg Gly Gly Ile Tyr Tyr Ser Thr Gln Asn Asp Tyr Asp
            100                 105                 110

Tyr Trp Gly Gln Gly Thr Gln Val Thr Val Ser Ser
        115                 120
```

<210> SEQ ID NO 65
<211> LENGTH: 123
<212> TYPE: PRT
<213> ORGANISM: Llama glama

<400> SEQUENCE: 65

Glu Val Gln Leu Val Glu Ser Gly Gly Gly Leu Val Gln Ala Gly Gly
1               5                   10                  15

Ser Leu Arg Leu Ser Cys Ala Val Ser Val Arg Thr Phe Ser Asp Tyr
            20                  25                  30

Arg Met Gly Trp Phe Arg Gln Ala Pro Gly Lys Glu Arg Glu Phe Val
        35                  40                  45

Ser Thr Ile Ser Trp Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Ala Gly Gly Gly Tyr Ala Gly Gly Thr Tyr Tyr His Pro Glu Glu
            100                 105                 110

Trp Gly Gln Gly Thr Gln Val Thr Val Ser Ser
        115                 120

<210> SEQ ID NO 66
<211> LENGTH: 127
<212> TYPE: PRT
<213> ORGANISM: Llama glama

<400> SEQUENCE: 66

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Cys Ile Ala Trp Phe Arg Gln Ala Pro Gly Lys Glu Arg Glu Pro Val
        35                  40                  45

Ser Cys Ile Thr Thr Ser Asp Gly Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Arg Leu Lys Pro Glu Asp Thr Ala Val Tyr Tyr Cys
                85                  90                  95

Ala Ala Tyr Phe Gly Tyr Gly Cys Tyr Gly Ala Gln Asp Tyr Arg
            100                 105                 110

Ala Met Asp Tyr Trp Gly Lys Gly Thr Leu Val Thr Val Ser Ser
        115                 120                 125

<210> SEQ ID NO 67
<211> LENGTH: 25
<212> TYPE: PRT
<213> ORGANISM: Llama glama

<400> SEQUENCE: 67

Glu Val Gln Leu Val Glu Ser Gly Gly Gly Leu Val Gln Ala Gly Asp
1               5                   10                  15

Ser Leu Arg Leu Ser Cys Ala Ala Ser
            20                  25

<210> SEQ ID NO 68
<211> LENGTH: 14
<212> TYPE: PRT
<213> ORGANISM: Llama glama

-continued

<400> SEQUENCE: 68

Trp Phe Arg Gln Ala Pro Gly Lys Glu Arg Glu Phe Val Ala
1               5                   10

<210> SEQ ID NO 69
<211> LENGTH: 32
<212> TYPE: PRT
<213> ORGANISM: Llama glama

<400> SEQUENCE: 69

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 70
<211> LENGTH: 11
<212> TYPE: PRT
<213> ORGANISM: Llama glama

<400> SEQUENCE: 70

Trp Gly Gln Gly Thr Gln Val Thr Val Ser Ser
1               5                   10

<210> SEQ ID NO 71
<211> LENGTH: 315
<212> TYPE: PRT
<213> ORGANISM: Homo Sapiens

<400> SEQUENCE: 71

Met Leu Ser Leu Leu His Ala Ser Thr Leu Ala Val Leu Gly Ala Leu
1               5                   10                  15

Cys Val Tyr Gly Ala Gly His Leu Glu Gln Pro Gln Ile Ser Ser Thr
            20                  25                  30

Lys Thr Leu Ser Lys Thr Ala Arg Leu Glu Cys Val Val Ser Gly Ile
        35                  40                  45

Thr Ile Ser Ala Thr Ser Val Tyr Trp Tyr Arg Glu Arg Pro Gly Glu
    50                  55                  60

Val Ile Gln Phe Leu Val Ser Ile Ser Tyr Asp Gly Thr Val Arg Lys
65                  70                  75                  80

Glu Ser Gly Ile Pro Ser Gly Lys Phe Glu Val Asp Arg Ile Pro Glu
                85                  90                  95

Thr Ser Thr Ser Thr Leu Thr Ile His Asn Val Glu Lys Gln Asp Ile
            100                 105                 110

Ala Thr Tyr Tyr Cys Ala Leu Trp Glu Ala Gln Gln Glu Leu Gly Lys
        115                 120                 125

Lys Ile Lys Val Phe Gly Pro Gly Thr Lys Leu Ile Ile Thr Asp Lys
    130                 135                 140

Gln Leu Asp Ala Asp Val Ser Pro Lys Pro Thr Ile Phe Leu Pro Ser
145                 150                 155                 160

Ile Ala Glu Thr Lys Leu Gln Lys Ala Gly Thr Tyr Leu Cys Leu Leu
                165                 170                 175

Glu Lys Phe Phe Pro Asp Val Ile Lys Ile His Trp Glu Glu Lys Lys
            180                 185                 190

Ser Asn Thr Ile Leu Gly Ser Gln Glu Gly Asn Thr Met Lys Thr Asn
        195                 200                 205

Asp Thr Tyr Met Lys Phe Ser Trp Leu Thr Val Pro Glu Lys Ser Leu
    210                 215                 220

```
Asp Lys Glu His Arg Cys Ile Val Arg His Glu Asn Asn Lys Asn Gly
225                 230                 235                 240

Val Asp Gln Glu Ile Ile Phe Pro Pro Ile Lys Thr Asp Val Ile Thr
            245                 250                 255

Met Asp Pro Lys Asp Asn Cys Ser Lys Asp Ala Asn Asp Thr Leu Leu
        260                 265                 270

Leu Gln Leu Thr Asn Thr Ser Ala Tyr Tyr Met Tyr Leu Leu Leu Leu
            275                 280                 285

Leu Lys Ser Val Val Tyr Phe Ala Ile Ile Thr Cys Cys Leu Leu Arg
        290                 295                 300

Arg Thr Ala Phe Cys Cys Asn Gly Glu Lys Ser
305                 310                 315

<210> SEQ ID NO 72
<211> LENGTH: 292
<212> TYPE: PRT
<213> ORGANISM: Homo Sapiens

<400> SEQUENCE: 72

Met Gln Arg Ile Ser Ser Leu Ile His Leu Ser Leu Phe Trp Ala Gly
1               5                   10                  15

Val Met Ser Ala Ile Glu Leu Val Pro Glu His Gln Thr Val Pro Val
            20                  25                  30

Ser Ile Gly Val Pro Ala Thr Leu Arg Cys Ser Met Lys Gly Glu Ala
        35                  40                  45

Ile Gly Asn Tyr Tyr Ile Asn Trp Tyr Arg Lys Thr Gln Gly Asn Thr
    50                  55                  60

Met Thr Phe Ile Tyr Arg Glu Lys Asp Ile Tyr Gly Pro Gly Phe Lys
65                  70                  75                  80

Asp Asn Phe Gln Gly Asp Ile Asp Ile Ala Lys Asn Leu Ala Val Leu
                85                  90                  95

Lys Ile Leu Ala Pro Ser Glu Arg Asp Glu Gly Ser Tyr Tyr Cys Ala
            100                 105                 110

Cys Asp Thr Leu Gly Met Gly Gly Glu Tyr Thr Asp Lys Leu Ile Phe
        115                 120                 125

Gly Lys Gly Thr Arg Val Thr Val Glu Pro Arg Ser Gln Pro His Thr
    130                 135                 140

Lys Pro Ser Val Phe Val Met Lys Asn Gly Thr Asn Val Ala Cys Leu
145                 150                 155                 160

Val Lys Glu Phe Tyr Pro Lys Asp Ile Arg Ile Asn Leu Val Ser Ser
                165                 170                 175

Lys Lys Ile Thr Glu Phe Asp Pro Ala Ile Val Ile Ser Pro Ser Gly
            180                 185                 190

Lys Tyr Asn Ala Val Lys Leu Gly Lys Tyr Glu Asp Ser Asn Ser Val
        195                 200                 205

Thr Cys Ser Val Gln His Asp Asn Lys Thr Val His Ser Thr Asp Phe
    210                 215                 220

Glu Val Lys Thr Asp Ser Thr Asp His Val Lys Pro Lys Glu Thr Glu
225                 230                 235                 240

Asn Thr Lys Gln Pro Ser Lys Ser Cys His Lys Pro Lys Ala Ile Val
                245                 250                 255
```

```
His Thr Glu Lys Val Asn Met Met Ser Leu Thr Val Leu Gly Leu Arg
            260                 265                 270

Met Leu Phe Ala Lys Thr Val Ala Val Asn Phe Leu Leu Thr Ala Lys
        275                 280                 285

Leu Phe Phe Leu
    290
```